(12) United States Patent
Tirosh et al.

(10) Patent No.: US 9,784,731 B2
(45) Date of Patent: Oct. 10, 2017

(54) METHODS OF MONITORING AND ANALYZING METABOLIC ACTIVITY PROFILES DIAGNOSTIC AND THERAPEUTIC USES OF SAME

(71) Applicant: Ramot at Tel-Aviv University Ltd., Tel-Aviv (IL)

(72) Inventors: Reuven Tirosh, Kfar-Saba (IL); Fernando Patolsky, Rechovot (IL); Hagit Peretz-Soroka, Ramat-Gan (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 195 days.

(21) Appl. No.: 14/280,612

(22) Filed: May 18, 2014

(65) Prior Publication Data
US 2014/0255972 A1    Sep. 11, 2014

Related U.S. Application Data

(63) Continuation of application No. 13/817,543, filed as application No. PCT/IL2012/050125 on Apr. 4, 2012, now Pat. No. 8,728,758.

(60) Provisional application No. 61/472,213, filed on Apr. 6, 2011.

(51) Int. Cl.
*G01N 33/50* (2006.01)
*G01N 33/84* (2006.01)
*G06F 19/12* (2011.01)

(52) U.S. Cl.
CPC ..... *G01N 33/5091* (2013.01); *G01N 33/5005* (2013.01); *G01N 33/5023* (2013.01); *G01N 33/5038* (2013.01); *G01N 33/5094* (2013.01); *G01N 33/84* (2013.01); *G06F 19/12* (2013.01)

(58) Field of Classification Search
CPC ........... G01N 33/5005; G01N 33/5023; G01N 33/5038; G01N 33/5091; G01N 33/5094; G01N 33/84; G06F 19/12
See application file for complete search history.

(56) References Cited

U.S. PATENT DOCUMENTS

| | | | |
|---|---|---|---|
| 2009/0305319 A1 * | 12/2009 | Baudenbacher ... | G01N 33/5005 435/29 |
| 2011/0059861 A1 | 3/2011 | Nolan et al. | |
| 2013/0224789 A1 | 8/2013 | Tirosh et al. | |

FOREIGN PATENT DOCUMENTS

| | | | |
|---|---|---|---|
| CN | 101213455 | 7/2008 | |
| DE | WO 2011000572 A1 * | 1/2011 | ............ C07K 7/56 |
| EP | 1736780 | 12/2006 | |
| JP | 2006-132989 | 5/2006 | |
| WO | WO 2008/018905 | 2/2008 | |
| WO | WO 2011/000572 | 1/2011 | |
| WO | WO 2012/137207 | 10/2012 | |

OTHER PUBLICATIONS

Henning (2004) Anti-Cancer Drugs 15(1): 7-14.*
Otto et al. (2003) Cancer Detect. and Prevent. 27(4): 291-296.*
Wu et al. (2007) Am. J. Physiol. Cell Physiol. 292(1): C125-136.*
Hynes et al. (2009) Anal. Biochem. 390(1): 21-28.*
Sprague et al. (2006) Clin. Lab. 52(7-8): 375-384.*
Office Action Dated Sep. 4, 2014 From the State Intellectual Property Office of the People's Republic of China Re. Application No. 201280022396.9 and Its Translation Into English.
Search Report Dated Sep. 4, 2014 From the State Intellectual Property Office of the People's Republic of China Re. Application No. 201280022396.9 and Its Translation Into English.
Notice of Reason for Rejection Dated Dec. 4, 2015 From the Japanese Patent Office Re. Application No. 2014-503276 and Its Translation Into English.
International Preliminary Report on Patentability Dated Oct. 17, 2013 From the International Bureau of WIPO Re. Application No. PCT/IL2012/050125.
International Search Report and the Written Opinion Dated Sep. 6, 2012 From the International Searching Authority Re. Application No. PCT/IL2012/050125.
Official Action Dated Aug. 1, 2013 From the US Patent and Trademark Office Re. U.S. Appl. No. 13/817,543.
Hartung et al. "Flow Cytometric Analysis of BCL-2 Can Distinguish Small Numbers of Acute Lymphoblastic Leukaemia Cells From B-Cell Precursors", British Journal of Haematology, 127: 50-58, 2004.
Henning et al. "Relevance of Tumor Microenvironment for Progression, Therapy and Drug Development", Anti-Cancer Drugs, XP009162065, 15(1): 7-14, Jan. 2004.
Huang et al. "Gene Expression Analysis With an Integrated CMOS Microarray by Time-Resolved Fluorescence Detection", Biosensors & Bioelectronics, 26(5): 2660-2665, Jan. 15, 2011.
Hynes et al. "In Vitro Analysis of Cell Metabolism Using a Long-Decay pH-Sensitive Lanthanide Probe and Extracellular Acidification Assay", Analytical Biochemistry, XP026130719, 390(1): 21-28, Jul. 1, 2009. p. 22, 1-h Col., Para 4-p. 23, 1-h Col., Para 3, Abstract.
Naume et al. "Detection of Isolated Tumor Cells in Peripheral Blood and in BM: Evaluation of a New Enrichment Method", Cytotherapy, 6(3): 244-252, 2004.
Oertel et al. "Immunocytochemical Methods in Haematology and Oncology", Journal of Cancer Research and Clinical Oncology, 126(8): 425-440, Aug. 2000.

(Continued)

Primary Examiner — Lisa J Hobbs

(57) ABSTRACT

A method of measuring a metabolic activity (MA) of a cell is provided. The method comprising independently measuring in an extracellular environment of the cell, time-dependent acidification profiles due to secretion of:
(i) non-volatile soluble metabolic products;
(ii) non-volatile soluble metabolic products and volatile soluble metabolic products; and
(iii) volatile soluble metabolic products;
wherein at least one of the time dependent acidification profiles is indicative of the metabolic activity of the cell. Also provided are clinical methods which make use of the assay.

14 Claims, 13 Drawing Sheets
(10 of 13 Drawing Sheet(s) Filed in Color)

(56) References Cited

OTHER PUBLICATIONS

Otto et al. "Microphysiological Testing for Chemosensitivity of Living Tumor Cells With Multiparametric Microsensor Chips", Cancer Detection and Prevention, XP002682126, 27(4): 291-296, 2003. p. 292, 1-h Col., Para 2-p. 293, 1-h Col., Para 2, Fig.1, Abstract.

Sprague et al. "Multiparametric Sensor-Chip Based Technology for Monitoring Metabolic Activity: A Proof-of-Principle Study With Live Tissue", Clinical Laboratory, XP009162068, 52(7-8): 375-384, 2006. p. 376, r-h Col., Last Para-p. 381, 1-h Col., Para 1, Fig.1, Abstract.

Wong et al. "Detection of Circulating Tumour Cells and Nodal Metastasis by Reverse Transcriptase-Polymerase Chain Reaction Technique", British Journal of Surgery, 84(6): 834-839, Jun. 1997.

Wu et al. "Multiparameter Metabolic Analysis Reveals a Close Link Between Attenuated Mitochondrial Beioenergetic Function and Enhanced Glycolysis Dependency in Human Tumor Cells", American Journal of Physiology, Cell Physiology, XP008082046, 292(1): C125-C136, Jan. 1, 2007. p. C126, 1-h Col., Para 4-p. C127, r-h Col., Para 2, Fig.1, Abstract.

* cited by examiner

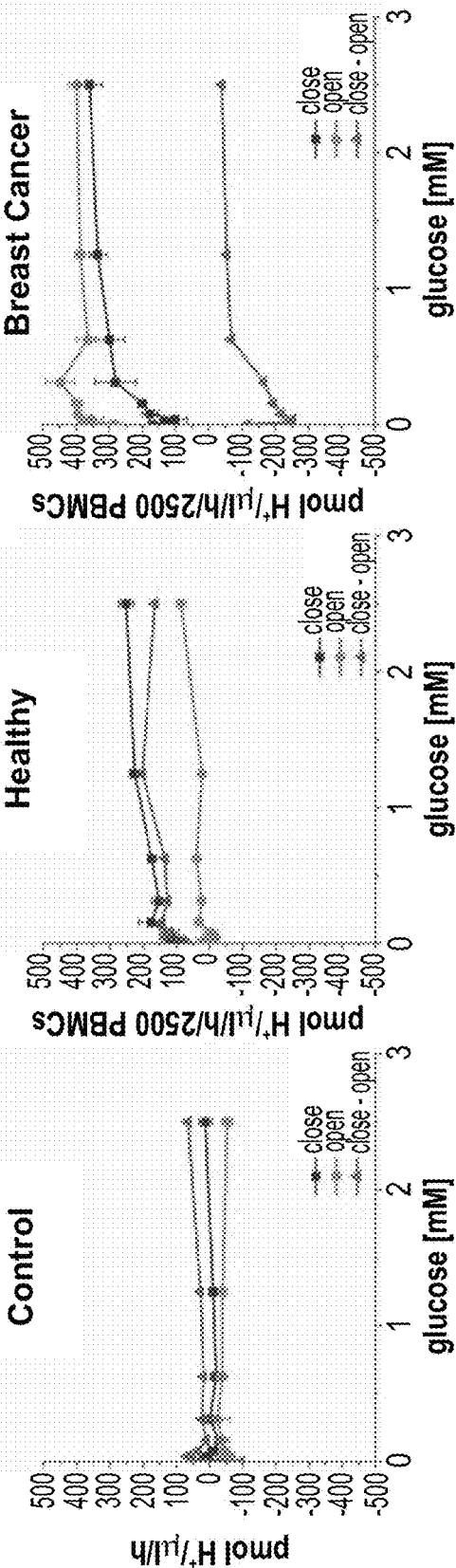

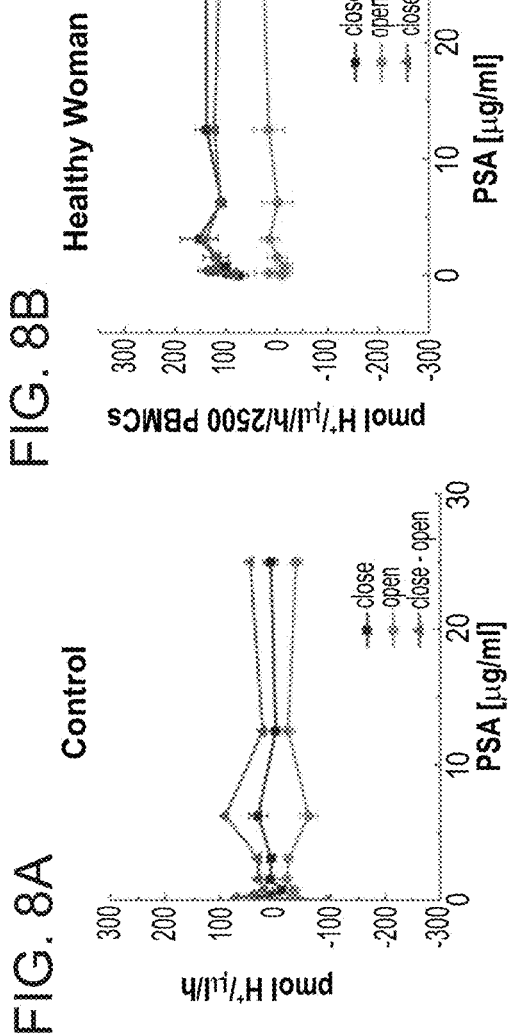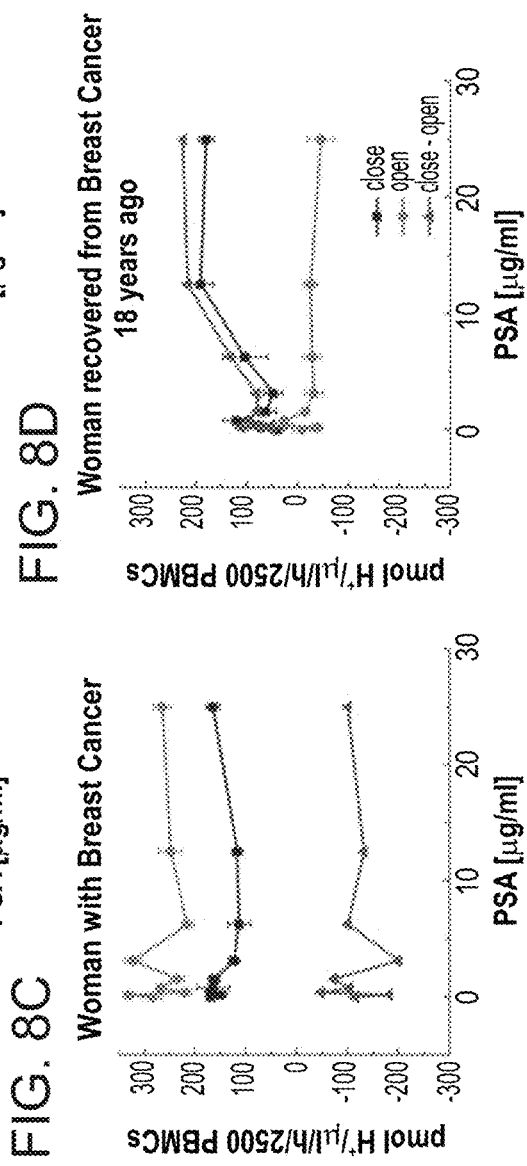

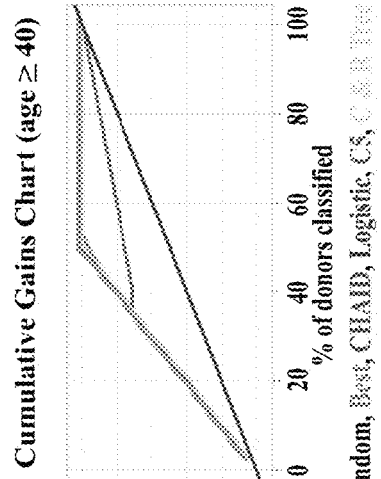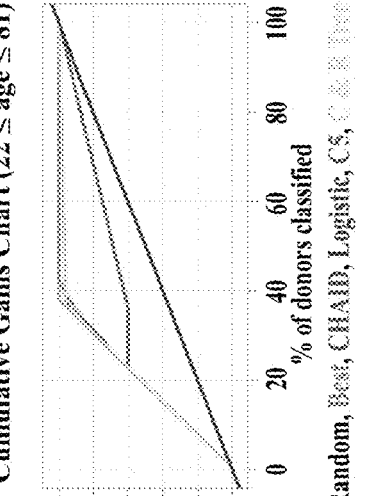

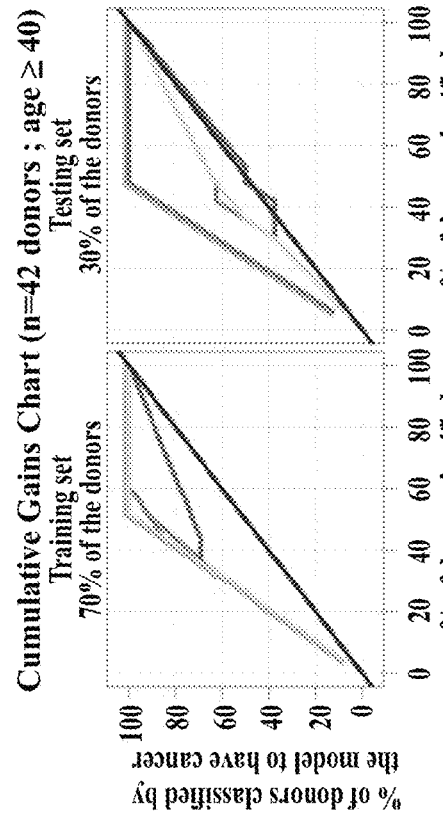
FIG. 10A
FIG. 10B
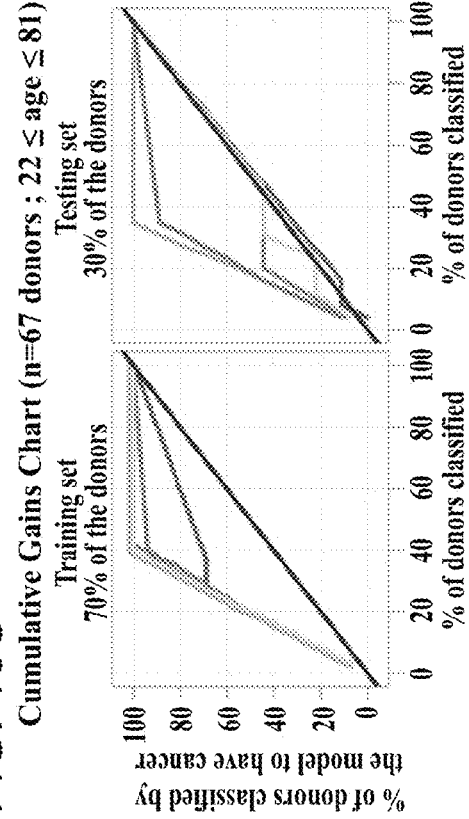
FIG. 10C
FIG. 10D

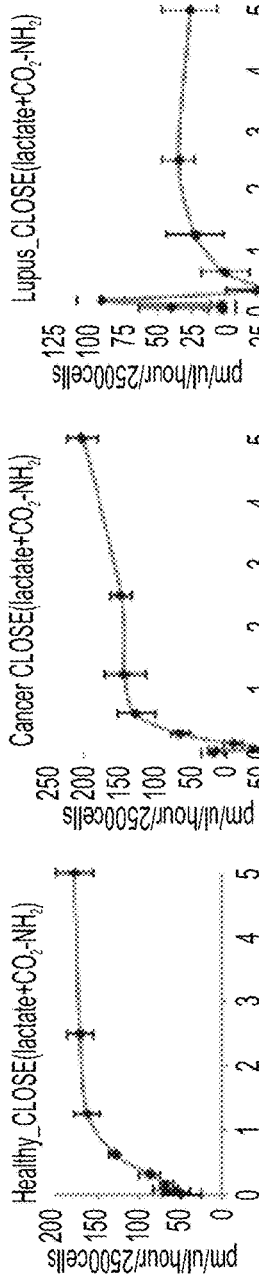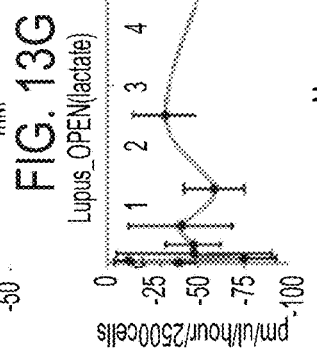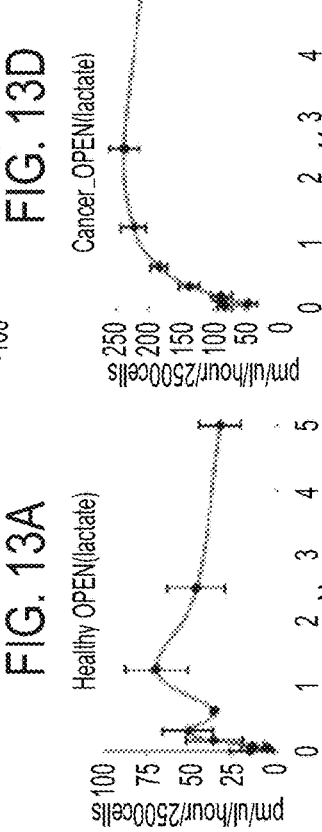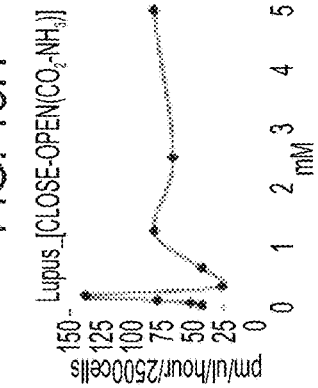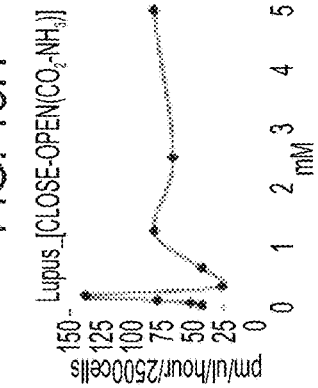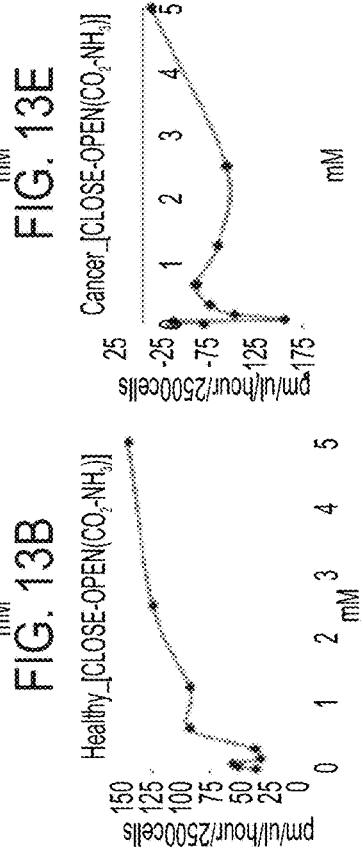

METHODS OF MONITORING AND ANALYZING METABOLIC ACTIVITY PROFILES DIAGNOSTIC AND THERAPEUTIC USES OF SAME

RELATED APPLICATIONS

This application is a continuation of U.S. patent application Ser. No. 13/817,543 filed on Feb. 19, 2013, which is a National Phase of PCT Patent Application No. PCT/IL2012/050125 having International filing date of Apr. 4, 2012, which claims the benefit of priority under 35 USC §119(e) of U.S. Provisional Patent Application No. 61/472,213 filed on Apr. 6, 2011. The contents of the above applications are all incorporated by reference as if fully set forth herein in their entirety.

FIELD AND BACKGROUND OF THE INVENTION

The present invention, in some embodiments thereof, relates to methods of monitoring and analyzing metabolic activity profiles and diagnostic or therapeutic uses of same, or specifically relates to cancer diagnosis by metabolic activity monitoring of blood samples.

A major problem in disease treatment remains early detection and staging. Early detection enables therapeutic treatment from the onset of the disease resulting in successful treatment in many cases. Staging of a disease might indicate on the appropriate protocol of medication which might be decisive for optimal treatment. For example today, millions of people are living with cancer or have had cancer. Cancer is the second most common cause of death in the United States, exceeded only by heart disease. Cancer accounts for nearly 1 out of every 4 deaths in the United States. The sooner a cancer is diagnosed and treated, the better the survival chances are.

All known methods for detection of cancer focus on identifying mostly the malignant tissue and/or its pathological cancer biomarkers secreted to the circulation. However, these diagnostic methods are only unfortunately effective at relatively advanced stages of the disease.

The Warburg effect is the observation that most cancer cells predominantly produce energy by a high rate of glycolysis followed by lactic acid production n in the cytosol, rather than by a comparatively low rate of glycolysis followed by oxidation of pyruvate in mitochondria like most normal cells [Kim J W, Dang C V (2006). "Cancer's molecular sweet tooth and the Warburg effect". *Cancer Res.* 66 (18): 8927-30]. Second, in 1920s Otto Warburg found that cancer cells[19,20], in contrast to normal differentiated cells, primarily rely on aerobic glycolysis rather than on mitochondrial oxidative phosphorylation to generate ATP as the fuel for energy needed for cellular processes. This historical phenomenon was termed "the Warburg effect"[21]. Otto Warburg postulated that this change in metabolism is the fundamental cause of cancer [Warburg O (1956). "On the origin of cancer cells". *Science* 123 (3191): 309-14], a claim now known as the Warburg hypothesis. About 50 years later the Warburg effect was also observed in activated lympocytes in vitro see e.g., MacIver et al. 2008 J. Leukocyte Biology 84:1-9; and DeBerardinis Cell Metabolism 7:11-20. The Warburg effect was found also in the immune system where activated T cells[22,23] rapidly hyperinduce glycolysis, for example by over-expression of glucose transporters (GLUT)[24].

The Warburg effect has important medical applications, as high aerobic glycolysis by malignant tumors is utilized clinically to diagnose and monitor treatment responses of cancers by imaging uptake of 2-$^{18}$F-2-deoxyglucose (FDG) (a radioactive modified hexokinase substrate) with positron emission tomography (PET). See also WO2007/102146. However, these methods are cumbersome and expensive by requiring high-tech facilities or in-situ tissue biopsies.

Therefore, non-invasive methods for early and simple diagnosis are needed.

SUMMARY OF THE INVENTION

According to an aspect of some embodiments of the present invention there is provided a method of measuring a metabolic activity (MA) of a cell, the method comprising independently measuring in an extracellular environment of the cell, time-dependent acidification profiles due to secretion of:
(i) non-volatile soluble metabolic products;
(ii) non-volatile soluble metabolic products and volatile soluble metabolic products;
(iii) volatile soluble metabolic products;
wherein at least one of the time dependent acidification profiles is indicative of the metabolic activity of the cell.

According to an aspect of some embodiments of the present invention there is provided a method of diagnosing a disease associated with a modified metabolic activity in a subject-in-need thereof, the method comprising:
(a) providing a biological sample of the subject which comprises a cell;
(b) independently measuring in an extracellular environment of the cell time-dependent acidification profiles due to secretion of:
(i) non-volatile soluble metabolic products;
(ii) non-volatile soluble metabolic products and volatile soluble metabolic products; and
(iii) volatile soluble metabolic products;
wherein at least one of the time dependent acidification profiles is indicative of the metabolic activity of the cell and whereas a shift in the metabolic activity compared to that of a normal unaffected cell sample examined under identical conditions is indicative of a disease associated with modified metabolic activity.

According to an aspect of some embodiments of the present invention there is provided a method of individually optimizing disease treatment, the method comprising:
(a) contacting a biological sample of the subject which comprises a cell with at least one medicament;
(b) independently measuring in an extracellular environment of the cell time-dependent acidification profiles due to secretion of:
(i) non-volatile soluble metabolic products;
(ii) non-volatile soluble metabolic products and volatile soluble metabolic products; and
(iii) volatile soluble metabolic products;
wherein at least one of the time dependent acidification profiles is indicative of the metabolic activity of the cell and whereas a shift in the metabolic activity of the cells towards that of a normal healthy cell sample examined under identical conditions is indicative of an efficacious medicament for the disease.

According to an aspect of some embodiments of the present invention there is provided a method of monitoring disease treatment in a subject, the method comprising:
(a) administering at least one medicament against the disease to the subject;

(b) retrieving a biological sample which comprises a cell of the subject following the administering;
(c) independently measuring in an extracellular environment of the cell time-dependent acidification profiles due to secretion of:
(i) non-volatile soluble metabolic products;
(ii) non-volatile soluble metabolic products and volatile soluble metabolic products; and
(iii) volatile soluble metabolic products;
wherein at least one of the time dependent acidification profiles is indicative of the metabolic activity of the cell and whereas a shift in the metabolic activity of the cells towards that of a normal healthy cell sample examined under identical conditions is indicative of an efficacious treatment of the disease.

According to an aspect of some embodiments of the present invention there is provided a method of disease treatment in a subject in need thereof, the method comprising:
(a) diagnosing a presence of the disease in the subject according to the method of claim 2;
(b) treating the subject based on the diagnosis.

According to an aspect of some embodiments of the present invention there is provided a method of identifying an agent capable of altering a metabolic activity of cells, the method comprising:
(a) subjecting cells to an agent;
(b) measuring the metabolic activity of the cells following (a) and optionally prior to (a) according to the method of claim 1, wherein a shift in the acidification profiles is indicative of an agent capable of altering a metabolic activity of cells.

According to some embodiments of the invention, the extracellular environment comprises a defined solution having a calibrated buffer capacity.

According to some embodiments of the invention, the buffer comprises a phosphate buffered saline.

According to some embodiments of the invention, the cell comprises a leukocyte.

According to some embodiments of the invention, the cells comprise a cancer cell.

According to some embodiments of the invention, the cells comprise a peripheral blood mononuclear cell (PBMC).

According to some embodiments of the invention, the disease comprises cancer.

According to some embodiments of the invention, the biological sample comprises a blood sample.

According to some embodiments of the invention, the disease is selected from the group consisting of cancer, pathogenic infection and an autoimmune disease.

According to some embodiments of the invention, the measuring is effected using a non-toxic membrane impermeable probe selected from the group consisting of a pH probe, a $CO_2$ probe and $NH_3$ probe and a lactate probe.

According to some embodiments of the invention, the pH probe comprises a ratiometric pH probe.

According to some embodiments of the invention, the pH probe comprises HPTS.

According to some embodiments of the invention, the non-volatile metabolites comprise lactate.

According to some embodiments of the invention, the volatile metabolites comprise $NH_3$ and $CO_2$.

According to some embodiments of the invention, the measuring acidification profile of (i) is effected in air-exposed chambers.

According to some embodiments of the invention, the measuring acidification profile of (ii) is effected in air-sealed chambers.

According to some embodiments of the invention, the measuring acidification profiles is effected at a constant temperature.

According to some embodiments of the invention, the constant temperature comprises 37° C.

According to some embodiments of the invention, the method further comprises subjecting the cell to a stimulant or inhibitor prior to, or concomitant with measuring the acidification profile.

According to some embodiments of the invention, the stimulant or inhibitor comprises a cell.

According to some embodiments of the invention, the stimulant or inhibitor comprises a cell-free antigen.

According to some embodiments of the invention, the stimulating cell comprises a lymphocytes and the cell comprises a non-syngeneic lymphocyte with respect to the lymphocyte.

According to some embodiments of the invention, the measuring acidification profiles is effected in commercial fluorescence multi well plate scanner.

According to some embodiments of the invention, signal to noise filtering of the MA test background measures is carried out by k-means cluster analysis.

According to some embodiments of the invention, the diagnostic decisions by the metabolic activity measures are subject to at least two decision tree models.

According to some embodiments of the invention, the decision tree models are selected from the group of C5, C&R Tree and CHAID.

According to some embodiments of the invention, the method further comprises separating the cell from the extracellular environment.

According to some embodiments of the invention, the separating is by ficoll separation under centrifugation.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIG. 1 is a schematic representation of the differences between oxidative phosphorylation, anaerobic glycolysis, and aerobic glycolysis (also known as the "Warburg effect").

FIG. 2 is a graph showing pH-dependent absorption spectra of 8-hydroxypyrene-1,3,6-trisulfonic acid (HPTS).

FIGS. 3A-D are graphs showing pH and acidity calibration of working solution at 2 mM and 10 mM phosphate buffers saline, at 1 µM HPTS. OPEN; The acidification steps were monitored at 37° C. without seal. CLOSE; The acidification steps were monitored at 37° C. after the multi-well plate was sealed.

X axis; The Ratio: (Fluorescence Intensity at Ex. 403 nm)/(Fluorescence Intensity at Ex. 455 nm.)

Right Y axis (triangles): The accumulated quantity of HCl (µmol/ml) as obtained by the sequential addition of 1N HCl.

Figure 3A:
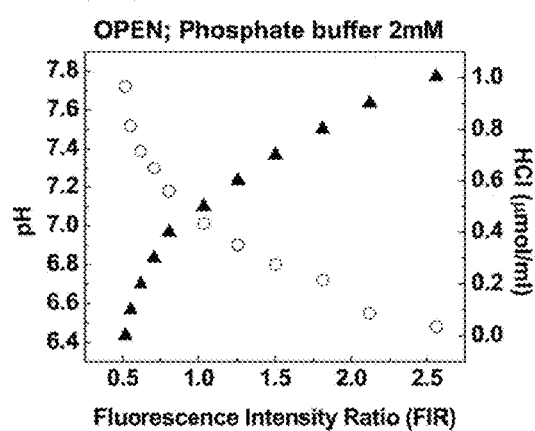
Figure 3B:
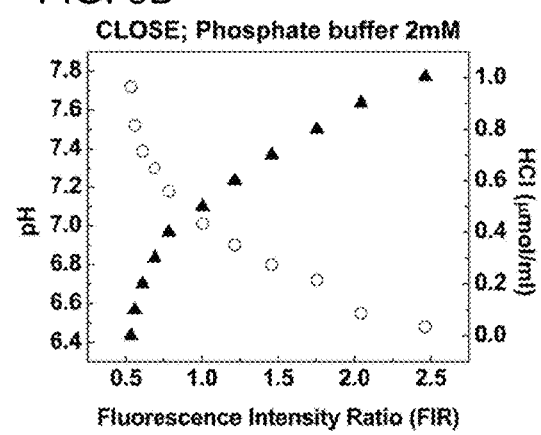
Figure 3C:
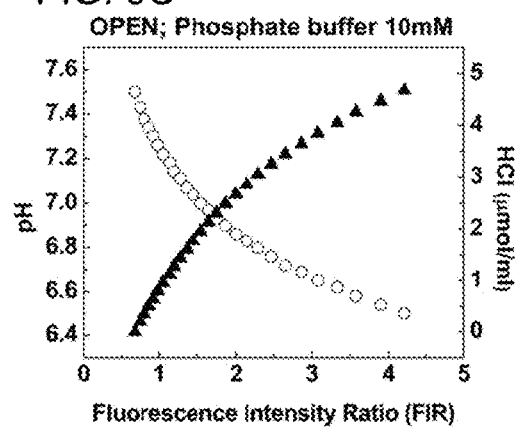
Figure 3D:
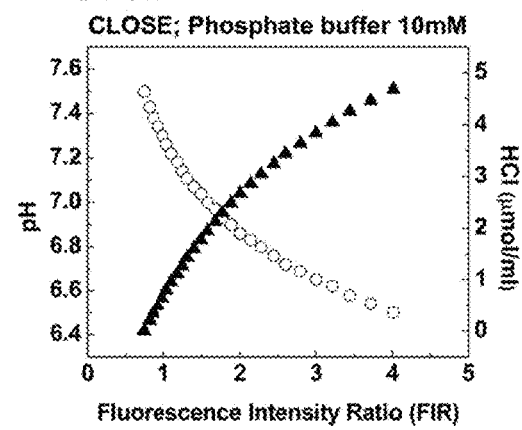

Left Y axis (circles): The appropriate pH values as measured by pH glass electrode. FIGS. 3A-B—Working solution with 2 mM phosphate buffer saline. FIGS. 3C-D—Working solution with 10 mM phosphate buffer saline.

Figure 4A:
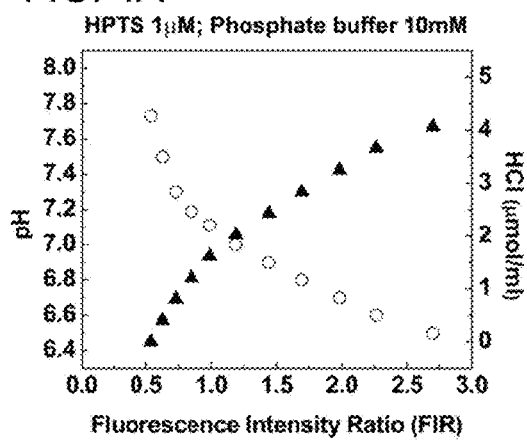
Figure 4B:
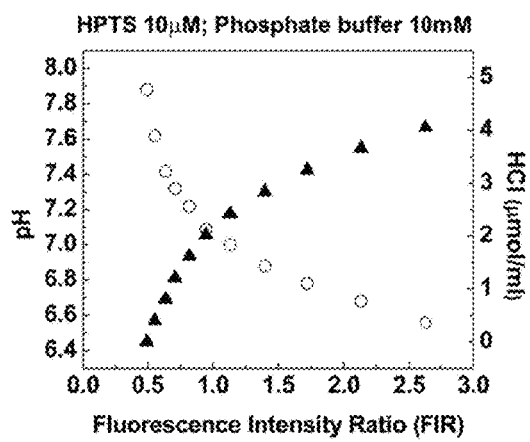

FIGS. 4A-B are graphs showing calibration curves at HPTS concentrations of 1 µM and 10 µM at 10 mM phosphate buffer saline.

X axis: The Ratio: (Fluorescence Intensity at Ex. 403 nm)/(Fluorescence Intensity at Ex. 455 nm.)

Right Y axis (triangles): The accumulated quantity of HCl (µmol/ml) as obtained by the sequential addition of 1N HCl.

Left Y axis (circles): The appropriate pH values as measured by pH glass electrode. (FIG. 4A) Final concentration of HPTS is 1 µM. (FIG. 4B) Final concentration of HPTS is 10 µM.

Figure 5A:
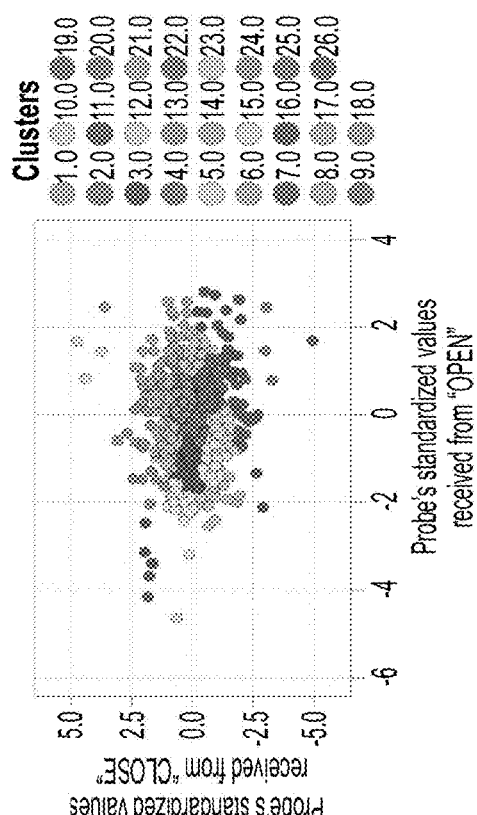
Figure 5B:
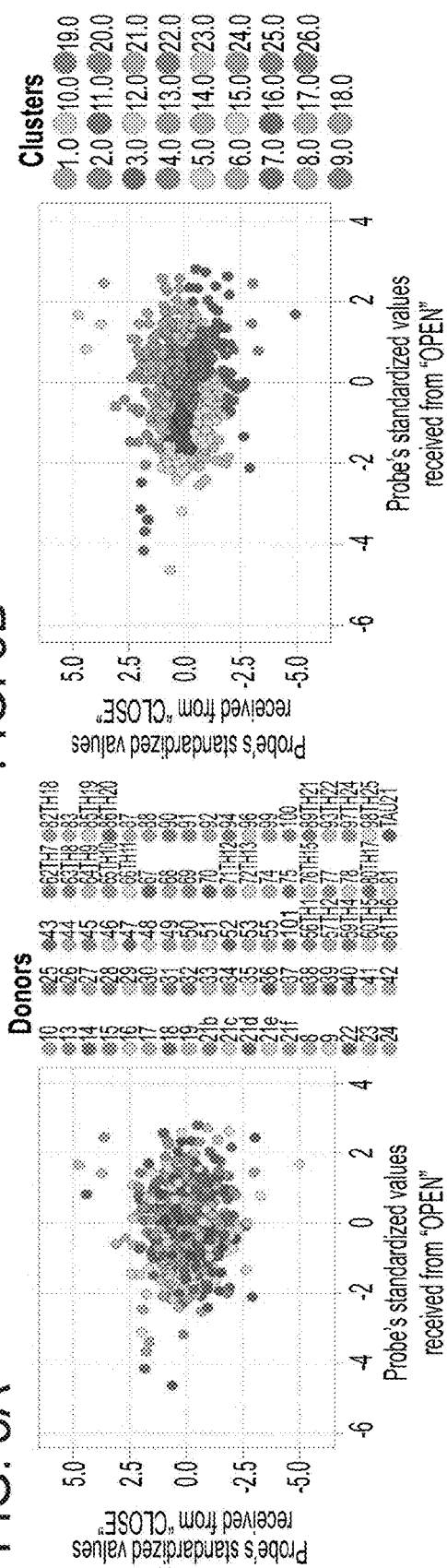
Figure 5D:
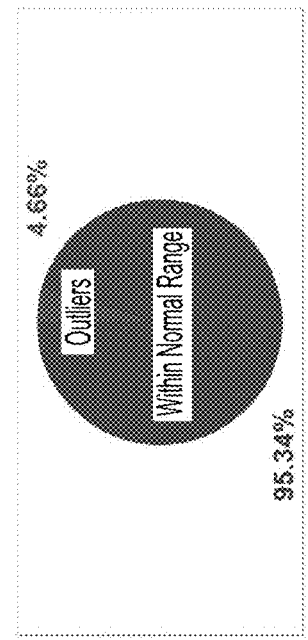
Figure 5C:
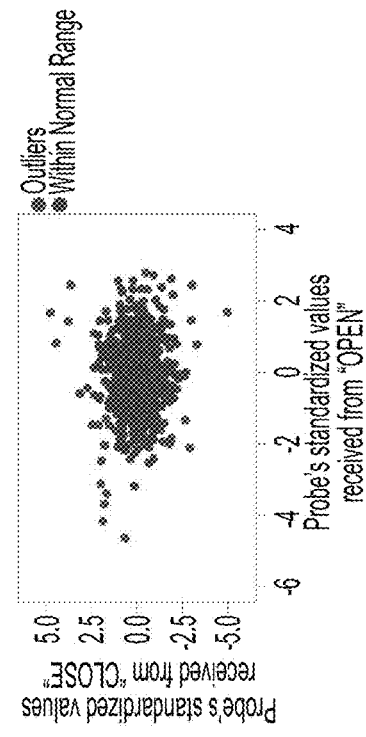

FIGS. 5A-D show k-means cluster analysis of the HPTS reference rate Values. FIGS. 5A-C—x-axis point on probe's standardized values received from "OPEN", and y-axis point on probe's standardized values received from "CLOSE" measurements. FIG. 5A—Examination of all values from all tests donors (N=730 observations) before cluster analysis. FIG. 5B—k-means cluster analysis of probe data indicates on 26 clusters presented with different colors. Five clusters were found small (observations ≤6) and therefore were discarded (outliers). FIGS. 5C-D—34 observations (4.66%) from 730 observations were excluded (red). The remaining 696 observations (95.34%) (blue) are presented in 21 separate clusters in (FIG. 5B). Then the mean values of "OPEN" and mean values of "CLOSE" states were recalculated for each donor.

FIGS. 6A-C are MA profiles for increasing glucose concentration obtained for typical healthy and cancer donors x axis: Glucose concentration (mM). y axis: Metabolic activity rate of hPBMCs in units of picomolH+/µl/hour/2500 PBMCs for FIGS. 6B-C and picomolH+/µl/hour for FIG. 6C. The acidification kinetics is measured during 1 hour of incubation at 37° C. "OPEN" state cycle of the multi well plate during 30 minutes. In this state there is gas ventilation of $CO_2$ and $NH_3$, so that only lactate acid production (including other non-volatile organic acids) contributes to the equivalent acidic accumulation in each well. "CLOSE" state cycle of the same multi well plate during 30 minutes. In this hermetically sealed state, $CO_2$ and $NH_3$ react at equilibrium with water to form carbonic acid and ammonium ions. The acidity level is produced by both the lactic and carbonic acid anions around pH 7.3. The $NH_4^+$ basic cation is evaluated here to titrate the acidity level. "CLOSE"-"OPEN"=$CO_2$+(—$NH_3$)). (FIG. 6A) a control record of the MA test including the probe HPTS and glucose, but without cells. (FIG. 6B) MA profiles of a 45 years old female representing a typical healthy donor (similar profiles are obtained for different age and gender). (FIG. 6C) MA profiles of a 37 years old female with Breast idc cancer at stage 2 and before treatment. Note induced MA changes between healthy and diseased samples may be detected already in the basal state (control sample without stimulants).

Figure 7A:
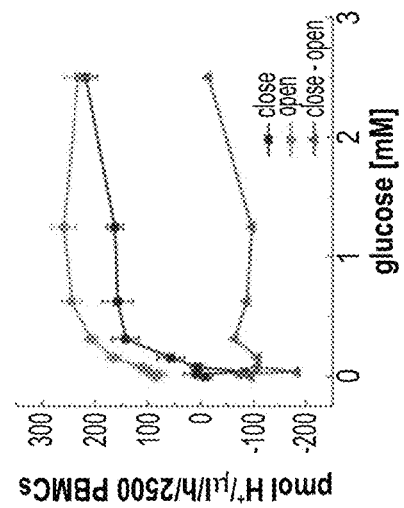
Figure 7B:
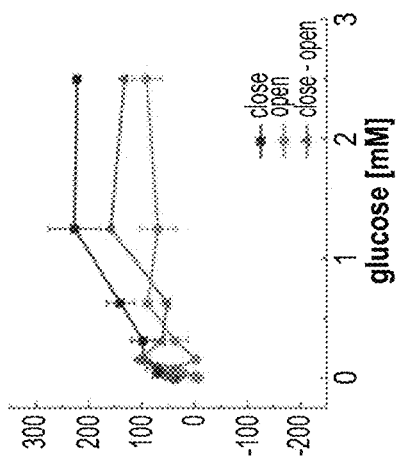
Figure 7C:
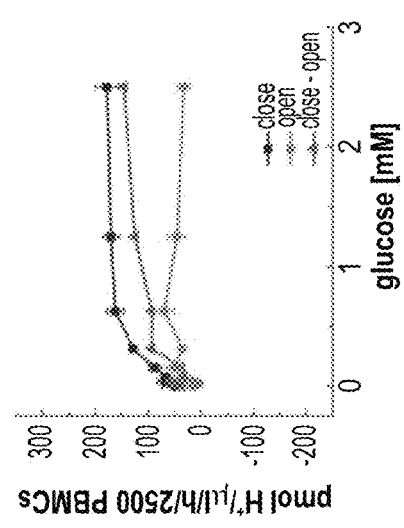
Figure 7D:
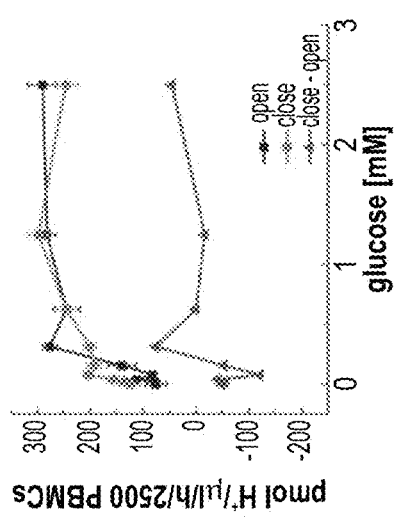

FIGS. 7A-D are graphs showing a case study follow-up of MA profiles for increasing glucose obtained for a 65 years old female with breast cancer compare to a 69 years old healthy male. Black—"CLOSE"; Red—"OPEN"; Blue—"C-O"="CLOSE"-"OPEN". FIGS. 7A—MA profiles of peripheral blood mononuclear cells (PBMCs) of a 69 years old healthy male. FIGS. 7B-D show 3 follow-up MA profiles of peripheral blood mononuclear cells (PBMCs) of a 65 years old female with breast idc cancer. X axis: Glucose concentration (mM). Y axis: Metabolic activity rate of PBMCs in units of picomol/µl/hour/2500 PBMCs. (FIG. 7B) The first MA test of the follow-up patient, already suspicious by the test results to have cancer (time=0). (FIG. 7C) time=+10.5 months—The second MA test just after routine mammography diagnosed by the physicians to have breast idc Cancer in stage 3. (FIG. 7D) time=+14.5 months—The sixth MA test was carried out after surgical removal of tumor of 2.2×2.4 cm in left breast and after 2 months of 3 chemotherapy treatments.

FIGS. 8A-D are graphs showing MA profiles for increasing PSA concentration obtained for typical healthy donors, breast cancer patient and breast cancer recovered donor.

FIG. 8A—a control record of the MA test including the probe HPTS and PSA, but without cells (FIGS. 8B-D) MA profiles of peripheral blood mononuclear cells (PBMCs) of 3 different donors. X axis: PSA concentration (µg/ml). Y axis: metabolic activity rate of PBMCs in units of picomole H+/µl/hour/2500 PBMCs for FIGS. 9B-D and picomole H+/µl/hour for FIG. 8A. The acidification kinetics is measured during 1 hour of incubation at 37° C. Black—"CLOSE"; Red—"OPEN"; Blue—"C-O"="CLOSE"-"OPEN". (FIG. 8A) MA profiles of a 59 years old female, representing a typical healthy donor. (FIG. 8B) MA profiles of a 37 years old female with breast idc cancer in stage 2 and before any treatment. (FIG. 8C) MA profiles of a 50 years old female recovered from breast cancer 18 years prior to the MA test.

FIGS. 9A-D show model building and classification evaluation for the MA test results.

FIGS. 9A-B—First group of donors in the age above 40 (n=42). FIGS. 9C-D—Second group of donors in the age between 22 to 81 years old. FIGS. 9A, C—The two tables present the best models with the best cutting point of the best classification. "O" refers to "OPEN" state, "C" refers to "CLOSE" state and "C-O" refers to "CLOSE-OPEN" state. TP refers to true positive, FN refers to false negative, TN refers to true negative and FP refers to false positive FIGS. 9 B,D—two graphs for the evaluation and comparison of the models performance by the cumulative gain charts. The y axis shows the percentage of donors classified by the models to have cancer. This is a percentage of the total donors (healthy and cancer patients). The x axis shows the percentage of patients classified to have cancer, which is a fraction of the 42 total donors for the first group and 67 total donors for the second group. Presented are the 4 best models that were able to classify with high accuracy both healthy donors and cancer patients. The fourth model is a logistic regression model from the family of regression models. Black line refer to random response rate (if randomly classified X % of donors, X % of cancer patients are obtained). Sky blue line refers to the theoretical best model. Red line refers to CHAID model, Green line refers to C5 algorithm, Yellow line refers to C&R tree model and Blue line refer to logistic model.

FIGS. 10A-D present evaluating model results of the MA test using a validation set of 30% of the donors. FIGS. 10A-B—First group of donors in the age above 40 (n=42). FIGS. 10C, D—Second group of donors in the age from 22 to 81 years old. (a, c) Data as described in FIG. 9 was randomly partitioned into two groups of "Training" and "Testing" using the clementine software V13.0. FIG. 10A—Validation set included 70% of the donors for the first group. FIG. 10C—Validation set included 70% of the donors for the second group. FIGS. 10A, C—Two graphs for the evaluation and comparison of the models performance made by the cumulative gains charts after random data partition. The y axis shows the percentage of donors classified by the models to have cancer. This is a percentage of the total donors (healthy & cancer patients). The x axis shows the percentage of patients classified to have cancer. The "Training" set are used to build the data mining model on 70% of the donors. The remaining 30% of the donors are later used to evaluate the classification result on the "Testing" set using the models that were generated in the training set (CHAID, Logistic, C5, C&R tree). As described in FIG. 9, sky blue line refers to the theoretical best model, Red line to CHAID model, Green line to C5 algorithm, Yellow line to C&R tree model, Blue line to logistic model and black line refers to random model. FIGS. 10B, D—The two tables present the best model with the best cutting point of the best classification after random data partition. "O" refers to "OPEN" state, "C" refers to "CLOSE" state and "C-O" refers to "CLOSE-OPEN" state. TP refers to true positive, FN refers to false negative, TN refers to true negative and FP refers to false positive. In both groups of donors C5 was the best performer in the "Testing" set while in the "Training" set C&R tree was the best performer.

Figure 11:
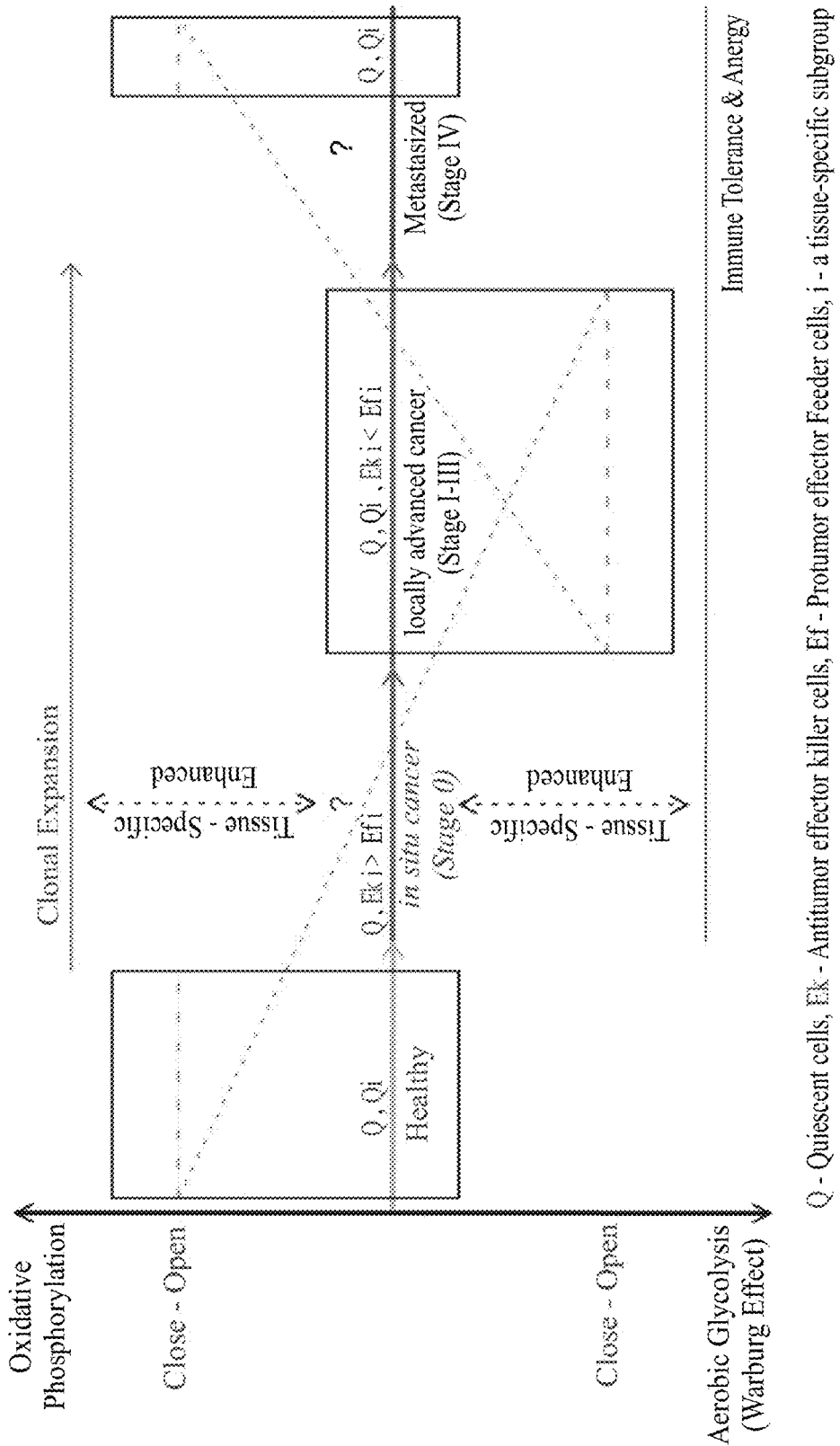

FIG. 11 depicts a working hypothesis: metabolic activity profiles of hPBMCs as a mirror image of tumor development. Cancer development is considered to be associated with changes in the physiological function of the immune system that might be reflected in different metabolic activity (MA) profiles of the hPBMCs. The Y axis presents the two arms of metabolic pathways', namely—oxidative phosphorylation versus aerobic glycolysis. The X axis presents the stages of tumor development from healthy to metastasized cancer. Quiescent cells (Q) have a dominant basal rate of oxidative phosphorylation. Under initial stages of tumor development there is "clonal expansion" of relevant tissue specific sub group of Q (Qi) into antitumor effector killer cells (Eki), which at later stages are probably transformed into protumor effector feeder cells (Efi). Concomitantly, immune tolerance and anergy succumb into the metastasized stage, where both tissue specific effector subgroups may be exhausted, including their respective quiescent subgroup (Qi). The present results reveal a metabolic shift from dominant oxidative phosphorylation preferred by hPBMCs of healthy donors to dominant aerobic glycolysis ("Warburg Effect") preferred by hPBMCs of various cancer patients at the stages of local tumor development (stage 1-3). The shift towards aerobic glycolysis may be related to a dominant Efi subgroup and possibly also Eki subgroup. The ability of tissue-specific early detection of cancer (stage 0) will be examined by a follow up protocol. It is expected to be revealed as enhanced/reduced metabolic activation under stimulation by tissue—specific antigens, compared to those obtained for healthy donors. In early metastasized cancer (stage 4) a gradual backward shift towards dominant oxidative phosphorylation is expected, yielding a diagnostic tool for the appropriate treatment. The above schematic description of characteristic metabolic activity profiles is presented by the striped orange line which is related to the difference "close-open" results of the MA test, which indicate the Warburg effect shift of hPBMCs.

Figure 12:
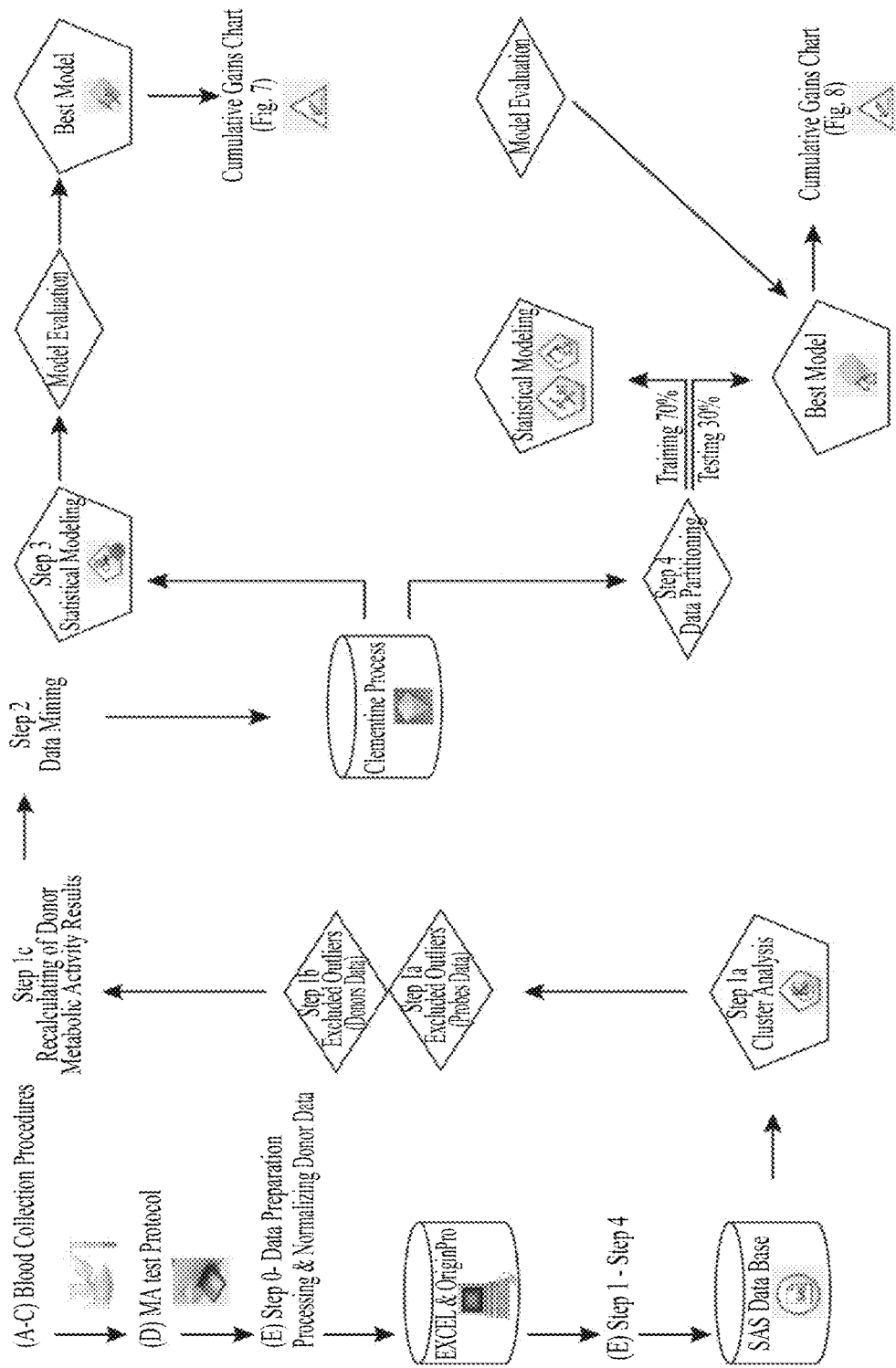

FIG. 12 is a flowchart of the MA test protocol and analysis framework. The sequential phases A-E of the MA test framework fit those detailed in Example 1 of the Examples section which follows.

FIGS. 13A-I MA Profiles for Increasing Glucose Concentration Obtained for typical healthy, cancer, and autoimmune lupus donors. X axis: Glucose concentration (mM). Y axis: Metabolic activity rate of PBMC in units of picomole $H^+$/ul/hour/2500 cells. The acidification kinetics is measured during 1 hour of incubation at 37° C.

FIGS. 13A, D, G—"CLOSE"; 13B, E, H—"OPEN"; 13C, F, I—"C-O"="CLOSE"-"OPEN". FIGS. 13A-C—Representative MA profiles of a typical healthy donor. FIGS. 13D-F—Representative MA profiles of a typical cancer patient. FIGS. 13G-I—MA profiles of a patient with systemic lupus (an autoimmune disease).

DESCRIPTION OF SPECIFIC EMBODIMENTS OF THE INVENTION

The present invention, in some embodiments thereof, relates to methods of monitoring and analyzing metabolic activity profiles and diagnostic or therapeutic uses of same, or specifically relates to cancer diagnosis by metabolic activity monitoring of blood samples.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Today, high-throughput methods are urgently required for early detection and staging of various diseases. For example, the sooner a cancer is found and treated, the better the survival chances are. Furthermore identifying the disease's stage ensures the appropriate treatment.

The present inventors have realized that in contrast to standard approaches for diseases detection that analyze various in situ parameters or relevant circulatory markers associated with the disease that allow disease detection at relatively late stages, the immune system might mirror disease state already at onset of the disease. Since the immune system is naturally responsible to combat disease development already at early stages it would be beneficial to identify characteristic profiles of relevant immune responses. Variation of such profiles of the metabolic activity of the immune system along with disease development may become useful also for disease staging. For example, in homeostasis, the immune system activity should be well controlled; hyperactivity is associated with autoimmune diseases while cancer development is probably related to hypoactivity of the immune system. These opposite routs might be indicated by general and more specific MA profiles in response to various nutrients and stimulants.

The present inventors have thus devised a ground-breaking, clinically-oriented approach for quantitative measurement of the metabolic activity of relevant cell populations, as an indicator of disease. The assay measures the rate of the metabolic activity of microliter cellular samples, by monitoring extracellular acidification using a pH-sensitive impermeable fluorescence probe.

As is illustrated in the Examples section which follows, using the metabolic activity (MA) analysis, the present inventors have revealed a significant shift between different metabolic pathways monitored on PBMCs obtained from cancer patients and healthy donors. This shift may be adopted as a diagnostic tool, for a clear-cut differentiation between healthy and cancer patients by monitoring characteristic changes in the metabolic activity of PBMCs (FIGS. 6-10, 13). These significant preliminary findings were obtained by comparing the MA test results in "open" versus "close" (air-sealed) wells. Both records enable to measure the accumulations of soluble versus volatile metabolic products (lactic acid versus $CO_2$ and $NH_3$), thereby differentiating between three metabolic pathways—oxidative phosphorylation, anaerobic glycolysis and aerobic glycolysis, as interpreted below.

Non activated T cells (naive T cells), like most normal differentiated cells, rely primarily on mitochondrial oxidative phosphorylation to efficiently generate ATP for the energy needed for cellular processes, and the volatile $CO_2$ product. In the absence of oxygen they must rely on much less efficient metabolic pathway of ATP production, associated with lactic acid production known as anaerobic glycolysis. In contrast, most cancer cells[18] are found to rely on aerobic glycolysis, which is similar to the anaerobic glycolysis despite the presence of oxygen. This phenomenon was originally found by Otto Warburg in relation to cancer cells, and termed "the Warburg effect". The present inventors revealed the presence of the "Warburg effect" in fresh PBMCs of cancer patients. Without being bound by theory, the immunometabolic rational of the "Warburg effect", namely the shift between naive and activated lymphocytes in fresh PBMCs of cancer patients, may be related to the need of aggressive and effective physiological function of activated T cells in the tumor cells neighborhood, where at early stages before angiogenesis it is probably oxygen deficient. This idea is consistent with the fact that tumor cells are initially adapted to oxygen deficiency through the "Warburg effect".

In light of the above metabolic pathways, the end products, $CO_2$ and lactate contribute directly to the acidification examined by the MA test.

Moreover, another end product which is considered to play a major role in the MA test is Ammonia ($NH_3$). One of the primary sources of cell energy is protein catabolism, which is the process of protein brake down to amino acids. Amino groups are removed from amino acids and converted to ammonia. Another source of cellular $NH_3$ production is through metabolic pathways of purines and pyrimidines making up the two groups of nitrogenous bases. In the present measurement system, as in vivo, vital cells must maintain the cytoplasm in a constant pH of about 7.2-7.4 by secretion of the metabolic acidic and basic products, such as lactic acid, carbonic acids and the ammonium base.

These findings already assure that by communicating with the immune system the physiologically-oriented MA analysis could have significant implications for developing new ways to detect, diagnose and treat cancer, as well as other diseases.

Thus, according to an aspect of the invention, there is provided a method of measuring a metabolic activity (MA) of a cell. The method comprising independently (i.e., separately) measuring in an extracellular environment of the cell, time-dependent acidification profiles due to secretion of:
(i) non-volatile soluble metabolic products;
(ii) non-volatile soluble metabolic products and volatile soluble metabolic products;
(iii) volatile soluble metabolic products;

wherein at least one of the time dependent acidification profiles is indicative of the metabolic activity pathway of the cells.

As used herein "metabolic activity pathway" refers to the relative contribution of mitochondrial oxidative phosphorylation, anaerobic glycolysis, aerobic glycolysis and $NH_3^+$ production to energy production.

The profiles may have a spike configuration or a monotonic saturated behavior.

A spikes profile typically reflects receptor mediated stimulation of metabolic activity which is expected to be more specific compared to the concentration dependent nutrient response. The latter response is generally a monotonic saturated profile.

As used herein "cell" refers to a prokaryotic or a eukaryotic cell for which the above metabolic activity can be measured. The cell can be a bacteria, yeast, plant, insect or mammalian cell. According to a specific embodiment, the cell is a human cell. It will be appreciated that the cell may refer to a single cell but may also refer to a plurality of cells. The cells may be isolated cells (having no tissue organization) or cells in a tissue or tissue fragment. According to a specific embodiment, when the cells are PBMCs, the assay is done on $10^3$-$10^{10}$ cells. According to a specific embodiment the number of cells is $10^6$-$10^7$.

The cell may be a differentiated cell, a non-differentiated cell (e.g., stem cell) or a dedifferentiated cell.

According to a specific embodiment, the cell is a cell of the immune system, that is a white blood cell (i.e., a leukocyte). Examples include, a neutrophil, an eosinophil, a basophil, a lymphocyte (T cell or B cell), a monocyte, a macrophage and a dendritic cell.

According to another embodiment, the cell is a pathogenic or diseased cell of any tissue such as a cancer cell. Other diseases and medical conditions which can be detected according to the present teachings are provided below.

Other cells which may be analyzed according to the present teachings include, but are not limited to, en embryonic cell (such as for WF qualification), a red blood cell, a platelet, a bacterial-infected cell, a fungus-infected cell, and a viral infected cell.

Thus, the cell may refer to an isolated population of cells which comprise a highly purified subset of specific cells i.e., homogenic cell population (e.g., >80% purity), e.g., T cells, or a heterogenic cell population which comprises various types of immune cells such as peripheral blood leukocytes (PBL) or mononuclear cells.

Cells may be non-cultured, cultured primary cells or cloned cells (e.g., cell-line).

The cells may be adherent cells or cells in suspension.

According to further embodiments, the cells can be non-genetically modified or genetically modified.

As used herein "independently measuring" refers to separate measuring of items (i), (ii) and possibly (iii). Although it will be appreciated, according to a specific embodiment, that (iii) is the result of subtracting (i) from (ii). These separate measurements can be performed in parallel, simultaneously, on identical yet separate cell samples, or sequentially on a single cell sample (as described in the Examples section which follows).

Thus, measuring extracellular acidification profile is performed by the calibrated curve of acidification (Table 1).

Measurement of metabolic activity is performed by calculating the accumulated acidification in relation to the fluorescencely measured pH changes in the extracellular environment of the cells (e.g., pmol/ul/hour/2500 cells) in "open" and "close" state. It will be appreciated that, according to a specific embodiment, this measurement is performed only in the extracellular environment of the cell and not intracellularly. Extracellular pH measurement is advantageous since in the extracellular environment there is a persistent acidic accumulation versus a relatively small average changes in the transient intracellular responses due to homeostatic physiological regulation; there is no physiological interference of the extracellular probe with intracellular processes; there is a comparative high signal to noise ratio of the extracellular ratiometric fluorescent probe; simplicity of fluorescent medium (calibrated buffer capacity) preparation versus cellular manipulations; there is no background fluorescence in contrast to significant leakage of intracellular probes; kinetic measurements are made with no need for permeabilization procedures, thereby allowing the analysis of live cells in real-time; there are minimal problems associated with quenching and oxidation effects; and finally simultaneous high throughput kinetic measurements are enabled without the above hurdles.

As used herein "an extracellular environment" of the cell refers to a natural environment e.g., blood or plasma, or an artificial environment such as a culture medium According to a specific embodiment, the MA test is effected in a defined solution (all components are known) having a calibrated buffered capacity.

It will be appreciated that the buffer capacity should ensure minor changes in the physiological pH.

According to a specific embodiment, the buffer is a phosphate buffer (e.g., phosphate buffer saline 1-10 mM or 10 mM phosphate buffer). It will be appreciated that low buffer concentration is required for acidification measurements at low cell concentration. According to a specific embodiment 10 mM phosphate buffer saline is used for $2.5 \times 10^6$ cells/ml.

Thus, kinetics of metabolic activity is monitored during the incubation by a minor acidification process of a HPTS fluorescence calibrated buffer capacity.

FIGS. 3A-D and 4A-D describe the working solution calibration and probe calibration, respectively.

According to a specific embodiment, measuring the acidification profiles is performed at a constant temperature, e.g., 20-40° C. or specifically, at optimal growth temperature, say 37° C. for mammalian cells.

As described hereinabove, the extracellular acidification profiles are indicative of the identity of the various metabolic products secreted by the cell.

Figure 1:
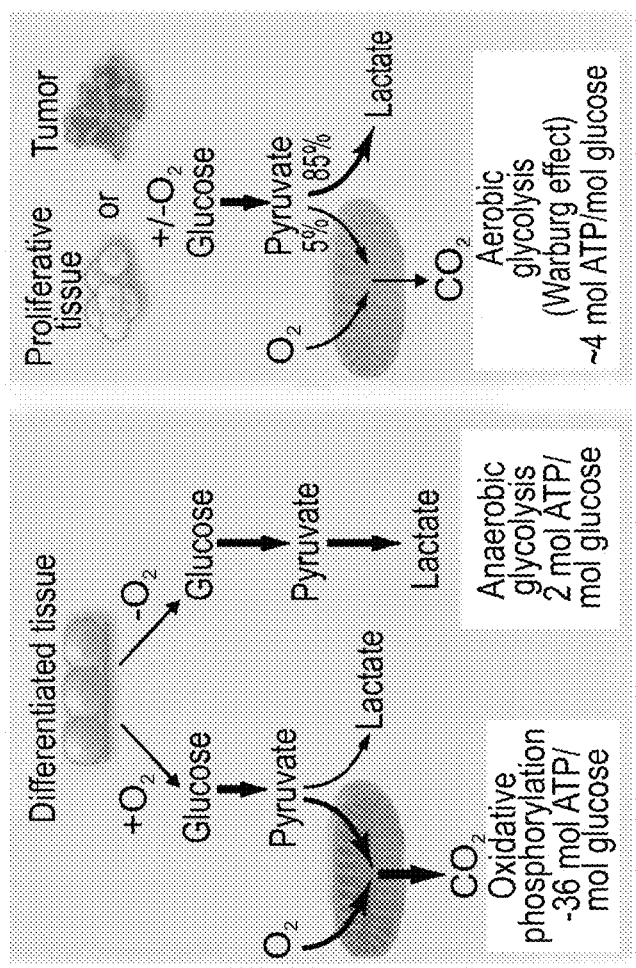
Figure 2:
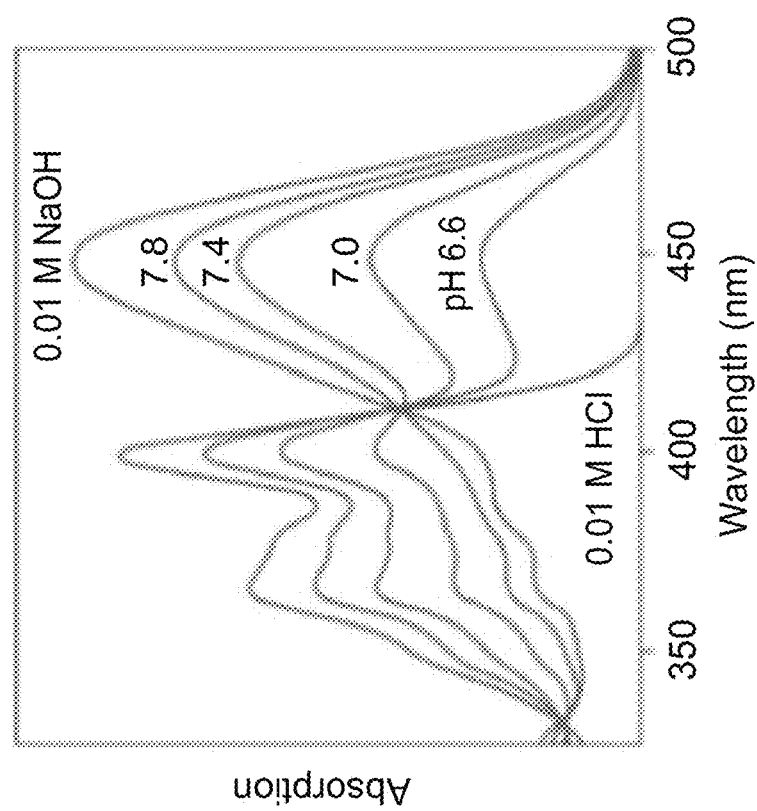

As shown in FIG. 1, a tumor or proliferative tissue (e.g., activated T cells) use preferentially aerobic glycolysis which is characterized mainly by the secretion of Lactate to the medium. In contrast, a differentiated tissue will employ oxidative phosphorylation or anaerobic glycolysis and therefore will secrete $CO_2$ or lactate, dependent on the availability of oxygen, respectively.

According to a specific embodiment, time dependent acidification profile due to secretion of non-volatile soluble metabolic products mainly lactate is performed in an air-exposed chamber. Under such conditions ("open"), there is gas ventilation of $CO_2$ and $NH_3$, so that only lactate acid production (including other non-volatile organic acids) contributes to the equivalent acidic accumulation in each well.

According to a specific embodiment, time dependent acidification profile due to secretion of non-volatile soluble metabolic products and volatile soluble metabolic products is effected in an air-sealed chamber. In the hermetically sealed state ("close"), $CO_2$ and $NH_3$ react at equilibrium with water to form carbonic acid and basic ammonium ions. In this state, however, the $NH_4^+$ basic cation titrates the acidity level produced by both the lactic and carbonic acid anions around pH 7.

According to a specific embodiment, the acidification kinetics is measured in 30 minutes sequence of air "open" and "closed" states of the multi well plate.

By the appropriate rates (V), of acidification (+) and basic titration (−), the total measured rates of acidification in the open state (Vopen) and the closed state (Vclosed) are described by the coupled equations:

$$Vopen=V(\text{lactic acid}).$$

$$Vclose=V(\text{lactic acid})+V(\text{carbonic acid})-V(\text{ammonium base}).$$

Using this configuration, the time-dependent acidification profile due to secretion of volatile soluble metabolic products is calculated by the subtraction of the profiles of (ii)-(i).

Measuring the kinetics of extracellular acidification is performed using a non-toxic membrane impermeable probe. Examples include, but are not limited to, a ratiometric pH probe, a $CO_2$ probe, an $NH_3$ probe, a lactate probe and a combination of same. According to a specific embodiment the ratiometric technique is required for the high sensitivity at pH buffered conditions.

Examples of specific probes which can be used according to the present teachings include, but are not limited to, HPTS, CFDA and carboxy fluorescein. Such probes are commercially available such as from Molecular Probes.

According to a specific embodiment, measuring the acidification is effected using the ratiometric pH probe 8-Hydroxypyrene-1,3,6-trisulfonic acid (HPTS).

HPTS is a cost effective, non-toxic, highly water-soluble membrane-impermeant pH indicator with a pKa of ~7.3 in aqueous buffers. HPTS exhibits a pH-dependent absorption shift, allowing ratiometric pH measurements as function of the ratio between the fluorescence intensities at 513 nm that are measured sequentially under excitation at 455 nm and 403 nm. This method is essential for the present sensitive measurements of minor pH changes in the physiological range around pH 7.

According to a specific embodiment. the fluorescent probe is attached to a nanoparticle, as nanosensors, in order to expand the ratiometric specific optical monitoring of various metabolic products: $CO_2$, $NH_3$, lactic acid etc. Intracellular fluorescence measurements are extremely useful in basic research of the physiological mechanisms of stimulation, e.g. for calcium mobilization and membrane depolarization. However, under the homeostatic cellular response, these intracellular stimulation signals become transient. Therefore they are considered much less suitable for sensitive monitoring of PBLs stimulation, compared to the ongoing accumulative extracellular acidification that is recorded in the MA test. Such extracellular monitoring may be better facilitated by attachment of ratiometric molecular optical probes to nanoparticles. Extracellular monitoring is biocompatible, minimizing negative effects common to intracellular probes measurements, pointing on the advantage of the extracellular methods not only in basic research but also for various clinical applications in different cell types.

The acidification profiles are presented by the rate of secretion of $H_2O$—$H^+$ equivalents, in units of picomole/μl/hour/2500 cells (see FIGS. 6-8, 13).

Any of the above acidification profiles can be used as an indicator of the metabolic activity of the cell. Alternatively, only one of the measured profiles is indicative of the metabolic activity of the cell.

As mentioned, the metabolic activity of the cell can be measured in naïve cells or activated/effector cells which have been exposed to different concentrations of a stimulant or an inhibitor.

As used herein a "stimulant" or an "inhibitor" refers to an entity that increases, decreases or changes a metabolic pathway of a cell in response thereto.

For instance, if the cell is a lymphocyte then the stimulant is an antigen that is recognized by the TCR or BCR and leads to clonal expansion or antibody production. Specific stimulants or inhibitors are listed in Table 1 below.

TABLE 1

| Units | Concentration | Role | |
|---|---|---|---|
| ug/ml | 0.4-50 | PHA-L is a potent mitogen for lymphocytes | H (PHA) |
| ug/ml | 0.8-100 | ConA is a lectin that binds to glycoproteins expressed on the T cell surface, thereby mimicking the T cell receptor activation which bypasses the requirement of co-stimulatory signals. | C (CONA) |
| ng/ml | 0.03-10 | Phorbol myristate acetate (PMA) mimic diacyglycerol and activates protein kinase C and thus eventually T cells. PMA acts selectively on a T-lymphocyte subpepulation that has high affinity for sheep erythrocytes (SRBC) and is distinct from that responsive to PHA. | P (PMA) |
| ng/ml | 0.03-10 | Lipopolysaccharide (LPS) strongly activates macrophages, monocytes and B cells. | S (LPS) |
| ug/ml | 0.4-50 | Myalin basic protein (MBP)-specific lymphocytes (CD4, CD8 cells, and NK cells (CD56+ CD3−)) (26) | M (MBP) (87-99aa) |
| ug/ml | 0.08-1 | A normal tissue antigen. This peptide (H-Ala-Ala-Gly-Ile-Gly-Ile-Leu-Thr-Val-OH) is the immunodominant epitope recognized by most melanoma-specific, cytoxic T lymphocytes (CTL). | N(MelanA) (27-35aa) |
| ug/ml | 0.4-50 | A normal prostate tissue specific antigen. This peptide is recognized by cytotoxic T lymphocytes (CTL). It is found as a biochemical marker of prostate cancer and breast cancer. | A(PSA) (146-154aa) |
| mM | 0.04-5 | It has been known for many years that lymphocytes and macrophages utilize glucose at a high rate, and until the important role of glutamine was identified, glucose was considered to the only fuel used to provide energy for cells of the immune system. | G (glucose) |
| mM | 0.03-4 | Glutamine is utilized at high rates by isolated cells of the immune system. It is an alternative energy source especially for cells that have high energy demands. | L (l-glutamine) |
| nM | 0.6-50 | Inhibits the mammalian target of rapamycin (Mtor) pathway by directly binding the mTOR Complex1 (Mtorc1). A recent study report that rapamycin might be particularly effective in blocking of activated T and B lymphocytes. Another study report that it selectively promotes activation and expansion of highly suppressive T regulatory cells. | R (Rapamycin) |

Other Examples are provided are provided hereinbelow.

The stimulant or inhibitor may be a cell or cell-associated stimulant or inhibitor. Examples of stimulating cells include, but are not limited to, leukocytes, stem cells, platelets, red blood cells, bacteria and fungi. Such a cellular stimulant or inhibitor may refer to an intact cell or a cell fragment e.g., cell membrane.

The use of a cell stimulant is specifically advantageous in mixed lymphocyte reactions (MLR) for use in transplantation applications such as for prediction of graft rejection (tissue matching), preventing or treating graft versus host disease or graft rejection. In such a case the stimulant is a lymphocyte that is non-syngeneic with respect to the cell.

Alternatively, the stimulant or inhibitor may be cell-free such as a cell-free antigen (e.g., soluble antigen, virus, a cellular biological fluid). Specific examples of cell-free stimulants or inhibitors, include, but are not limited to, metabolites, nutrients (e.g., glucose), mitogens, peptides, cytokines, hormones, vitamins, drugs, antibodies, neurotransmitters, cancer specific antigens and various disease-associated tissue-specific normal antigens (TNAs).

Specific examples of MHC-restricted antigens (peptides) include but are not limited to CEA (Carcinoembryonic Antigen), MUC-1, HER2, CD340, MAGE and prolactin (others are listed in Renkvist et al. 2001 "A listing of human tumor antigens recognized by T cells". Cancer Immunol. Immunotherapy 50:3-15.

The stimulant or inhibitor is contacted with the cell at various concentrations.

The stimulant or inhibitor is selected according to the suspected pathology. For example, in in-vitro fertilization applications the ongoing MA of the embryo secretions to it's extracellular fluid are examined. Alternatively or additionally, the MA stimulation profiles of the mother PBLs are examined by stimulation of the embryo secretions.

In screening tests, the cells are contacted with a plurality of stimulants or inhibitors, and the acidification profiles are concomitantly monitored for each such reaction.

Thus, the MA test, as described above can be performed on a limited number of samples (e.g., using a tissue culture dish) or on a plurality of samples, screening response to a plurality of stimulants/inhibitors or screening a plurality of samples from different patients or a combination of same. High throughput screening can be performed using a multi well plate, a multi well plate reader (for detecting the fluorescent signal), a CCD camera applying image analysis or fiber optics matrices.

According to an embodiment of the invention, the resultant acidification profiles are recorded and stored in a database such as on a computer readable medium so as to enable data manipulation and construction of computational models. As used herein, "computer readable medium" refers to any medium which can be read and accessed directly by a computer. Such media include, but are not limited to, magnetic storage media, such as floppy discs, hard disc storage medium, and magnetic tape; optical storage media such as optical discs or CD-ROM; electrical storage media such as RAM and ROM; and hybrids of these categories such as magnetic/optical storage media. Selection and use of appropriate storage media is well within the capabilities of one of ordinary skill in the art.

As used herein, "recorded" refers to a process of storing information on computer readable medium.

The robustness and accurateness of the present methodology suggests its use in numerous clinical applications.

Thus, according to an aspect of the invention there is provided a method of diagnosing a disease associated with a modified metabolic activity in a subject-in-need thereof, the method comprising:
(a) providing a biological sample of the subject which comprises a cell;
(b) independently measuring in an extracellular environment of the cell time-dependent acidification profiles due to secretion of:
(i) non-volatile soluble metabolic products;
(ii) non-volatile soluble metabolic products and volatile soluble metabolic products; and
(iii) volatile soluble metabolic products;
wherein at least one of the time dependent acidification profiles is indicative of the metabolic activity of the cell and whereas a shift in of the metabolic activity compared to that of a normal unaffected cell sample examined under identical conditions is indicative of a disease associated with modified metabolic activity.

The subject may be a healthy animal or a human subject undergoing a routine well-being check up. Alternatively, the subject may be at risk of having a disease associated with a modified metabolic activity such as cancer (e.g., a genetically predisposed subject, a subject with medical and/or family history of cancer, a subject who has been exposed to carcinogens, occupational hazard, environmental hazard) and/or a subject who exhibits suspicious clinical signs of cancer [e.g., blood in the stool or melena, unexplained pain, sweating, unexplained fever, unexplained loss of weight up to anorexia, changes in bowel habits (constipation and/or diarrhea), tenesmus (sense of incomplete defecation, for rectal cancer specifically), anemia and/or general weakness).

As used herein "a disease associated with a modified metabolic activity" refers to a disease that is characterized by a cell population that has undergone a shift in metabolic activity as compared to an identical cell population taken from a normal, healthy (unaffected with the disease). That cell population that has undergone a shift in metabolic activity, can be a pathogenic cell population (i.e., disease-causing cells e.g., cancer cells) or a non-pathogenic cell population (e.g., disease combating cells e.g., immune cells such as in the case of solid-tumor). For instance, as described hereinabove, in oncology, most cancer cells predominantly and some populations of the immune system undergoing clonal expansion produce energy by a high rate of glycolysis followed by lactic acid production in the cytosol, rather than by a comparatively low rate of glycolysis followed by oxidation of pyruvate in mitochondria like most normal cells (see FIG. 1).

Cellular biological samples which can be used in accordance with the present teachings include, but are not limited to, blood (e.g., peripheral blood leukocytes, peripheral blood mononuclear cells, whole blood, cord blood), a solid tissue biopsy, cerebrospinal fluid, urine, lymph fluids, and various external secretions of the respiratory, intestinal and genitourinary tracts, synovial fluid, amniotic fluid and chorionic villi.

Biopsies include, but are not limited to, surgical biopsies including incisional or excisional biopsy, fine needle aspirates and the like, complete resections or body fluids. Methods of biopsy retrieval are well known in the art.

As used herein the term "diagnosis" or "diagnosing" refers to determining presence or absence of a pathology (e.g., a disease, disorder, condition or syndrome), classifying a pathology or a symptom, determining a severity of the pathology, monitoring pathology progression, forecasting an outcome of a pathology and/or prospects of recovery and screening of a subject for a specific disease.

According to the instant teachings the acidification profiles of a normal, healthy (unaffected) sample of identical cell composition are determined under identical conditions which were used to monitor the cells of the subject.

Once acidification profiles are obtained (e.g., with or without stimulant/inhibitor), the profile(s) are recorded. A shift (i.e., a change) in the metabolic activity between the cells of the subject and those of the control (normal, unaffected), as evidenced from the acidification profiles obtained under identical conditions, is indicative of a disease associated with the modified metabolic activity profiles.

The results of the metabolic activity assay may be subject to decision tree models which classify the results and assist in final diagnosis. According to a preferred embodiment, at least two models are combined (see FIGS. 9 & 10). Examples of such models include, but are not limited to, CHAID, C5 and C&R Tree. The Logistic model may be further applied.

Examples of medical conditions which can be diagnosed and treated (as is further described hereinbelow) according to the present teachings include, but are not limited to, cancer, pathogenic infection and autoimmune diseases. Specific examples are provided infra.

Inflammatory Diseases

Include, but are not limited to, chronic inflammatory diseases and acute inflammatory diseases.

Inflammatory Diseases Associated with Hypersensitivity

Examples of hypersensitivity include, but are not limited to, Type I hypersensitivity, Type II hypersensitivity, Type III hypersensitivity, Type IV hypersensitivity, immediate hypersensitivity, antibody mediated hypersensitivity, immune complex mediated hypersensitivity, T lymphocyte mediated hypersensitivity and DTH.

Type I or immediate hypersensitivity, such as asthma.

Type II hypersensitivity include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann N Y Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); antifactor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like β-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau Y E. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

Type IV or T cell mediated hypersensitivity, include, but are not limited to, rheumatoid diseases, rheumatoid arthritis (Tisch R, McDevitt H O. Proc Natl Acad Sci USA 1994 Jan. 18; 91 (2):437), systemic diseases, systemic autoimmune diseases, systemic lupus erythematosus (Datta S K., Lupus 1998; 7 (9):591), glandular diseases, glandular autoimmune diseases, pancreatic diseases, pancreatic autoimmune diseases, Type 1 diabetes (Castano L. and Eisenbarth G S. Ann. Rev. Immunol. 8:647); thyroid diseases, autoimmune thyroid diseases, Graves' disease (Sakata S. et al., Mol Cell Endocrinol 1993 March; 92 (1):77); ovarian diseases (Garza K M. et al., J Reprod Immunol 1998 February; 37 (2):87), prostatitis, autoimmune prostatitis (Alexander R B. et al., Urology 1997 December; 50 (6):893), polyglandular syndrome, autoimmune polyglandular syndrome, Type I autoimmune polyglandular syndrome (Hara T. et al., Blood. 1991 Mar. 1; 77 (5):1127), neurological diseases, autoimmune neurological diseases, multiple sclerosis, neuritis, optic neuritis (Soderstrom M. et al., J Neurol Neurosurg Psychiatry 1994 May; 57 (5):544), myasthenia gravis (Oshima M. et al., Eur J Immunol 1990 December; 20 (12): 2563), stiff-man syndrome (Hiemstra H S. et al., Proc Natl Acad Sci USA 2001 Mar. 27; 98 (7):3988), cardiovascular diseases, cardiac autoimmunity in Chagas' disease (Cunha-Neto E. et al., J Clin Invest 1996 Oct. 15; 98 (8):1709), autoimmune thrombocytopenic purpura (Semple J W. et al., Blood 1996 May 15; 87 (10):4245), anti-helper T lymphocyte autoimmunity (Caporossi A P. et al., Viral Immunol 1998; 11 (1):9), hemolytic anemia (Sallah S. et al., Ann Hematol 1997 March; 74 (3):139), hepatic diseases, hepatic autoimmune diseases, hepatitis, chronic active hepatitis (Franco A. et al., Clin Immunol Immunopathol 1990 March; 54 (3):382), biliary cirrhosis, primary biliary cirrhosis (Jones D E. Clin Sci (Colch) 1996 November; 91 (5):551), nephric diseases, nephric autoimmune diseases, nephritis, interstitial nephritis (Kelly C J. J Am Soc Nephrol 1990 August; 1 (2):140), connective tissue diseases, ear diseases, autoimmune connective tissue diseases, autoimmune ear disease (Yoo T J. et al., Cell Immunol 1994 August; 157 (1):249), disease of the inner ear (Gloddek B. et al., Ann N Y Acad Sci 1997 Dec. 29; 830:266), skin diseases, cutaneous diseases, dermal diseases, bullous skin diseases, pemphigus vulgaris, bullous pemphigoid and pemphigus foliaceus.

Examples of delayed type hypersensitivity include, but are not limited to, contact dermatitis and drug eruption.

Examples of types of T lymphocyte mediating hypersensitivity include, but are not limited to, helper T lymphocytes and cytotoxic T lymphocytes.

Examples of helper T lymphocyte-mediated hypersensitivity include, but are not limited to, $T_h1$ lymphocyte mediated hypersensitivity and $T_h2$ lymphocyte mediated hypersensitivity.

Autoimmune Diseases

Include, but are not limited to, cardiovascular diseases, rheumatoid diseases, glandular diseases, gastrointestinal diseases, cutaneous diseases, hepatic diseases, neurological diseases, muscular diseases, nephric diseases, diseases related to reproduction, connective tissue diseases and systemic diseases.

Examples of autoimmune cardiovascular diseases include, but are not limited to atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), Wegener's granulomatosis, Takayasu's arteritis, Kawasaki syndrome (Praprotnik S. et al., Wien Klin Wochenschr 2000 Aug. 25; 112 (15-16):660), anti-factor VIII autoimmune disease (Lacroix-Desmazes S. et al., Semin Thromb Hemost. 2000; 26 (2):157), necrotizing small vessel vasculitis, microscopic polyangiitis, Churg and Strauss syndrome, pauci-immune focal necrotizing and crescentic glomerulonephritis (Noel L H. Ann Med Interne (Paris). 2000 May; 151 (3):178), antiphospholipid syndrome (Flamholz R. et al., J Clin Apheresis 1999; 14 (4):171), antibody-induced heart failure (Wallukat G. et al., Am J Cardiol. 1999 Jun. 17; 83 (12A):75H), thrombocytopenic purpura (Moccia F. Ann Ital Med Int. 1999 April-June; 14 (2):114; Semple J W. et al., Blood 1996 May 15; 87 (10):4245), autoimmune hemolytic anemia (Efremov D G. et al., Leuk Lymphoma 1998 January; 28 (3-4):285; Sallah S. et al., Ann Hematol 1997 March; 74 (3):139), cardiac autoimmunity in Chagas' disease (Cunha-Neto E. et al., J Clin Invest 1996 Oct. 15; 98 (8):1709) and anti-helper T lymphocyte autoimmunity (Caporossi A P. et al., Viral Immunol 1998; 11 (1):9).

Examples of autoimmune rheumatoid diseases include, but are not limited to rheumatoid arthritis (Krenn V. et al., Histol Histopathol 2000 July; 15 (3):791; Tisch R, McDevitt H O. Proc Natl Acad Sci units S A 1994 Jan. 18; 91 (2):437) and ankylosing spondylitis (Jan Voswinkel et al., Arthritis Res 2001; 3 (3): 189).

Examples of autoimmune glandular diseases include, but are not limited to, pancreatic disease, Type I diabetes, thyroid disease, Graves' disease, thyroiditis, spontaneous autoimmune thyroiditis, Hashimoto's thyroiditis, idiopathic myxedema, ovarian autoimmunity, autoimmune anti-sperm infertility, autoimmune prostatitis and Type I autoimmune polyglandular syndrome. diseases include, but are not limited to autoimmune diseases of the pancreas, Type 1 diabetes (Castano L. and Eisenbarth G S. Ann. Rev. Immunol. 8:647; Zimmet P. Diabetes Res Clin Pract 1996 October; 34 Suppl: S125), autoimmune thyroid diseases, Graves' disease (Orgiazzi J. Endocrinol Metab Clin North Am 2000 June; 29 (2):339; Sakata S. et al., Mol Cell Endocrinol 1993 March; 92 (1):77), spontaneous autoimmune thyroiditis (Braley-Mullen H. and Yu S, J Immunol 2000 Dec. 15; 165 (12): 7262), Hashimoto's thyroiditis (Toyoda N. et al., Nippon Rinsho 1999 August; 57 (8):1810), idiopathic myxedema (Mitsuma T. Nippon Rinsho. 1999 August; 57 (8):1759), ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), autoimmune prostatitis (Alexander R B. et al., Urology 1997 December; 50 (6):893) and Type I autoimmune polyglandular syndrome (Hara T. et al., Blood. 1991 Mar. 1; 77 (5):1127).

Examples of autoimmune gastrointestinal diseases include, but are not limited to, chronic inflammatory intestinal diseases (Garcia Herola A. et al., Gastroenterol Hepatol. 2000 January; 23 (1):16), celiac disease (Landau Y E. and Shoenfeld Y. Harefuah 2000 Jan. 16; 138 (2):122), colitis, ileitis and Crohn's disease.

Examples of autoimmune cutaneous diseases include, but are not limited to, autoimmune bullous skin diseases, such as, but are not limited to, pemphigus vulgaris, bullous pemphigoid and pemphigus foliaceus.

Examples of autoimmune hepatic diseases include, but are not limited to, hepatitis, autoimmune chronic active hepatitis (Franco A. et al., Clin Immunol Immunopathol 1990 March; 54 (3):382), primary biliary cirrhosis (Jones D E. Clin Sci (Colch) 1996 November; 91 (5):551; Strassburg C P. et al., Eur J Gastroenterol Hepatol. 1999 June; 11 (6):595) and autoimmune hepatitis (Manns M P. J Hepatol 2000 August; 33 (2):326).

Examples of autoimmune neurological diseases include, but are not limited to, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83; Oshima M. et al., Eur J Immunol 1990 December; 20 (12):2563), neuropathies, motor neuropathies (Kornberg A J. J Clin Neurosci. 2000 May; 7 (3):191); Guillain-Barre syndrome and autoimmune neuropathies (Kusunoki S. Am J Med Sci. 2000 April; 319 (4):234), myasthenia, Lambert-Eaton myasthenic syndrome (Takamori M. Am J Med Sci. 2000 April; 319 (4):204); paraneoplastic neurological diseases, cerebellar atrophy, paraneoplastic cerebellar atrophy and stiff-man syndrome (Hiemstra H S. et al., Proc Natl Acad Sci units S A 2001 Mar. 27; 98 (7):3988); non-paraneoplastic stiff man syndrome, progressive cerebellar atrophies, encephalitis, Rasmussen's encephalitis, amyotrophic lateral sclerosis, Sydeham chorea, Gilles de la Tourette syndrome and autoimmune polyendocrinopathies (Antoine J C. and Honnorat J. Rev Neurol (Paris) 2000 January; 156 (1):23); dysimmune neuropathies (Nobile-Orazio E. et al., Electroencephalogr Clin Neurophysiol Suppl 1999; 50:419); acquired neuromyotonia, arthrogryposis multiplex congenita (Vincent A. et al., Ann N Y Acad Sci. 1998 May 13; 841:482), neuritis, optic neuritis (Soderstrom M. et al., J Neurol Neurosurg Psychiatry 1994 May; 57 (5):544) and neurodegenerative diseases.

Examples of autoimmune muscular diseases include, but are not limited to, myositis, autoimmune myositis and primary Sjogren's syndrome (Feist E. et al., Int Arch Allergy Immunol 2000 September; 123 (1):92) and smooth muscle autoimmune disease (Zauli D. et al., Biomed Pharmacother 1999 June; 53 (5-6):234).

Examples of autoimmune nephric diseases include, but are not limited to, nephritis and autoimmune interstitial nephritis (Kelly C J. J Am Soc Nephrol 1990 August; 1 (2):140).

Examples of autoimmune diseases related to reproduction include, but are not limited to, repeated fetal loss (Tincani A. et al., Lupus 1998; 7 Suppl 2:S107-9).

Examples of autoimmune connective tissue diseases include, but are not limited to, ear diseases, autoimmune ear diseases (Yoo T J. et al., Cell Immunol 1994 August; 157 (1):249) and autoimmune diseases of the inner ear (Gloddek B. et al., Ann N Y Acad Sci 1997 Dec. 29; 830:266).

Examples of autoimmune systemic diseases include, but are not limited to, systemic lupus erythematosus (Erikson J. et al., Immunol Res 1998; 17 (1-2):49) and systemic sclerosis (Renaudineau Y. et al., Clin Diagn Lab Immunol. 1999 March; 6 (2):156); Chan O T. et al., Immunol Rev 1999 June; 169:107).

Infectious Diseases

Examples of infectious diseases include, but are not limited to, chronic infectious diseases, subacute infectious diseases, acute infectious diseases, viral diseases, bacterial diseases, protozoan diseases, parasitic diseases, fungal diseases, mycoplasma diseases and prion diseases.

Graft Rejection Diseases

Examples of diseases associated with transplantation of a graft include, but are not limited to, graft rejection, chronic graft rejection, subacute graft rejection, hyperacute graft rejection, acute graft rejection and graft versus host disease.

Allergic Diseases

Examples of allergic diseases include, but are not limited to, asthma, hives, urticaria, pollen allergy, dust mite allergy, venom allergy, cosmetics allergy, latex allergy, chemical allergy, drug allergy, insect bite allergy, animal dander allergy, stinging plant allergy, poison ivy allergy and food allergy.

According to a specific embodiment the disease is cancer.

Cancerous Diseases

Examples of cancer include but are not limited to carcinoma, lymphoma, blastoma, sarcoma, and leukemia. Particular examples of cancerous diseases but are not limited to: Myeloid leukemia such as Chronic myelogenous leukemia. Acute myelogenous leukemia with maturation. Acute promyelocytic leukemia, Acute nonlymphocytic leukemia with increased basophils, Acute monocytic leukemia. Acute myelomonocytic leukemia with eosinophilia; Malignant lymphoma, such as Birkitt's Non-Hodgkin's; Lymphoctyic leukemia, such as Acute lumphoblastic leukemia. Chronic lymphocytic leukemia; Myeloproliferative diseases, such as Solid tumors Benign Meningioma, Mixed tumors of salivary gland, Colonic adenomas; Adenocarcinomas, such as Small cell lung cancer, Kidney, Uterus, Prostate, Bladder, Ovary, Colon, Sarcomas, Liposarcoma, myxoid, Synovial sarcoma, Rhabdomyosarcoma (alveolar), Extraskeletel myxoid chonodrosarcoma, Ewing's tumor; other include Testicular and ovarian dysgerminoma, Retinoblastoma, Wilms' tumor, Neuroblastoma, Malignant melanoma, Mesothelioma, breast, skin, pancreas, cervix, prostate, and ovarian.

Thus, the present teachings can be used in disease detection. Following is a non-limiting embodiment which relates to early cancer detection.

The present teachings provide for an immune system-based approach as a non-invasive diagnostic tool for early detection and staging of cancer. Conventional diagnostic approaches are mainly focused on the pathology of malignant tissues and on cancer specific antigens and genes. In contrary, the present teachings focus on normal versus abnormal responses of the immune system as a naturally available tool for early detection and staging of cancer (as well as of other diseases). Thus, the present teachings provide for a high throughput functional physiological blood test by measurement of PBLs metabolic activity stimulation profiles (MASPs) of the immune system in response to a wide spectrum of stimulants/inhibitors at different concentrations (metabolites, nutrients, mitogens, natural and synthetic peptides, cytokines, hormones, vitamins, drugs, antibodies, neurotransmitters, cancer specific antigens and various disease-associated tissue-specific normal antigens (TNAs)). By conventional views of immunological responses relatively small effects are anticipated, even under "clonal expansion" of effector subpopulations of PBLs. However, in terms of "systems biology", a minor subgroup response may be amplified throughout network stimulation. It is suggested that the immune system combats cancer by its regular function in detecting abnormal high levels of TNAs. PBLs metabolic activity may also be used for diagnosis of advanced stages of cancer development. At the stage of local tumor, the effective killing response of the immune system is already limited, being unable to destroy the tumor tissue even though specific tumor infiltrating lymphocytes (TILs) are observed. Yet, in this stage such circulating T lymphocytes might be still responsible for killing separate circulating cancer cells. The shift from a local tumor to a metastatic-phase points on a complete specific failure of the immune system, and this transition might be measured by characteristic changes in the MA stimulation profiles.

Disease diagnosis made according to the present teachings is followed by substantiation of the screen results using gold standard methods. Once diagnosis is established either relying on the present teachings or substantiated using Gold standard methods, the subject is informed of the diagnosis and treated as needed.

It will be appreciated that the present teachings have a variety of applications pertaining to individually optimizing disease treatment, monitoring disease treatment in a subject, determining a treatment for a subject and identifying an agent capable of treating a disease associated with abnormal metabolic activity.

Thus, according to an aspect of the invention there is provided a method of disease treatment in a subject in need thereof, the method comprising:

(a) diagnosing a presence of the disease in the subject according to the method described above; and (b) treating the subject based on the diagnosis.

As used herein the term "treating" refers to abrogating, substantially inhibiting, slowing or reversing the progression of a condition, substantially ameliorating clinical or aesthetical symptoms of a condition or substantially preventing the appearance of clinical or aesthetical symptoms of a condition.

According to another aspect of the invention there is provided a method of individually optimizing disease treatment, the method comprising:

(a) contacting a biological sample of the subject which comprises a cell with at least one medicament;

(b) independently measuring in an extracellular environment of the cell time-dependent acidification profiles due to secretion of:

(i) non-volatile soluble metabolic products;

(ii) non-volatile soluble metabolic products and volatile soluble metabolic products; and (iii) volatile soluble metabolic products;

wherein at least one of the time dependent acidification profiles is indicative of the metabolic activity of the cell and whereas a shift in the metabolic activity of the cell towards that of a normal healthy cell sample examined under identical conditions is indicative of an efficacious medicament for the disease.

As used herein "individually optimizing treatment" refers to an ex vivo method of tailoring treatment regimen (e.g., type of medicament, dose).

As used herein a "medicament" refers to a formulation of a medicine, medicinal drug or medication, as interchangeably used herein. Examples of medicaments, include but are not limited to, chemotherapy, antibiotics, antiparasitic drugs, antiviral and the like.

As used herein, the term "contacting" refers to bringing the medicament into the vicinity of a cell under conditions such that the medicament contacts the cell membrane and if needed internalizes thereto. Thus, for example, the contacting should be effected under buffer conditions, at a temperature and time sufficient to allow the medicament to affect cell phenotype (e.g., cytotoxic or cytostatic effect). The contacting may be effected in vitro, ex vivo or in vivo. The contacting may be effected in a vessel which is also capable of detecting the product of the enzymatic reaction (i.e., in the electrochemical cell), such that the electrical signal is detected on-line. Such vessels are further described herein below. Alternatively, the contacting may be effected in a separate vessel from where the detection takes place such that it is possible to continuously withdraw samples at particular time points and place such samples within the electrochemical cells. Thus, the contacting may be effected in a test tube, flask, tissue culture, chip, array, plate, microplate, capillary, or the like. The cells may be placed on a vibrating plate following the addition of the substrate for continuous thorough mixing of the contents of the cells.

According to a specific embodiment, "a shift in the metabolic activity of the cell towards that of a normal healthy cell sample examined under identical conditions" refers to at least a 10% local or global (throughout the profile) shift preferably towards 100% identity to the control normal healthy cell sample.

A shift beyond a predetermined threshold as will be determined by the skilled artisan is indicative of an efficacious treatment.

Likewise, there is provided a method of monitoring disease treatment in a subject, the method comprising:
(a) administering at least one medicament against the disease to the subject;
(b) retrieving a biological sample which comprises a cell of the subject following the administering;
(c) independently measuring in an extracellular environment of the cell time-dependent acidification profiles due to secretion of:
(i) non-volatile soluble metabolic products;
(ii) non-volatile soluble metabolic products and volatile soluble metabolic products; and
(iii) volatile soluble metabolic products;
wherein at least one of the time dependent acidification profiles is indicative of the metabolic activity of the cell and whereas a shift in the metabolic activity of the cells towards that of a normal healthy cell sample examined under identical conditions is indicative of an efficacious treatment of the disease. For example, it is suggested that in the metastatic phase the MA profile might regress close to the normal profile.

Likewise, there is provided a method of identifying an agent capable of altering a metabolic activity of cells, the method comprising:
(a) subjecting cells to an agent;
(b) measuring the metabolic activity of the cells following (a) and optionally prior to (a) according to the method of claim 1, wherein a shift in the acidification profiles is indicative of an agent capable of altering a metabolic activity of cells.

As used herein, the term "agent" refers to a test composition comprising a biological agent or a chemical agent.

Examples of biological agents that may be tested as potential modulators of metabolic activity according to the method of the present invention include, but are not limited to, nucleic acids, e.g., polynucleotides, ribozymes, siRNA and antisense molecules (including without limitation RNA, DNA, RNA/DNA hybrids, peptide nucleic acids, and polynucleotide analogs having altered backbone structures or other chemical modifications); proteins, polypeptides (e.g. peptides), carbohydrates, lipids and "small molecule" drug candidates. "Small molecules" can be, for example, naturally occurring compounds (e.g., compounds derived from plant extracts, microbial broths, and the like) or synthetic organic or organometallic compounds having molecular weights of less than about 10,000 daltons, preferably less than about 5,000 daltons, and most preferably less than about 1,500 daltons.

According to a preferred embodiment of this aspect of the present invention the agents are anti-cancer, anti-viral or antibiotic agents.

Examples of conditions that may be tested as potential anti cancer agents according to the method of the present invention include, but are not limited to, radiation exposure (such as, gamma radiation, UV radiation, X-radiation).

It will be appreciated that the shift, as used herein, can be also a different level (e.g., higher level) of MA in same profile; a change in basal state, and/or a shift in the agent concentration that induces maximal MA effect.

Once an agent capable of altering a metabolic activity of cells has been identified along in accordance with the above teachings, the invention further comprises synthesizing the agent or purifying it from a natural source.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Experimental Procedures

A. Blood Donors Requirement and Blood Collection by Medical Experts

Blood samples were collected in Vacutubes 9 ml with EDTA (Greiner Bio-One 455036). The study was approved by the institutional Review Boards at the Sheba Medical Center (Ramat Gan Israel) and the Israeli Ministry of Health, (Helsinki Approval number 7780-10-SMC).

B. Collection of Donor's Demographic and Clinical Information

For the protection of confidentiality, all collected blood samples were labeled and immediately coded to be used in the database records and diagnostic analysis.

The MA test results were collected from 42 healthy donors and 25 cancer patients from 22 to 81 years old (Table 2). The healthy donors are a mixed population including treated cases of high blood pressure, high cholesterol levels, minor flu and inflammation.

TABLE 2

Clinical characteristics of cancer patients:
ac—adencocarcinoma, idc—invasive ductal carcinoma,
gej—gastroesphageal junction,
NSCLC—Non-small-cell lung carcinoma

| Tumor Stage | Tumor Type | Gender | Age | Patient Number |
|---|---|---|---|---|
| 1 | Breast idc | Female | 53 | 1 |
| 1 | Breast idc | Female | 64 | 2 |
| 2 | Breast idc | Male | 63 | 3 |
| 2 | Breast idc | Female | 37 | 4 |
| 2 | Breast idc | Female | 61 | 5 |
| 2 | Breast idc | Female | 38 | 6 |
| 2 | Breast idc | Female | 65 | 7 |
| 3 | Breast idc | Female | 32 | 8 |
| 3 | Breast idc | Female | 42 | 9 |
| 3 | NSCLC ac | Male | 46 | 10 |
| 4 | NSCLC ac | Male | 61 | 11 |
| 4 | NSCLC ac | Female | 60 | 12 |
| 4 | NSCLC ac | Male | 81 | 13 |
| 4 | Colon ac | Female | 70 | 14 |
| 4 | Colon | Female | 49 | 15 |
| 2 | Colon ac | Female | 56 | 16 |
| 2 | Rectum ac | Female | 52 | 17 |
| 4 | Rectum ac | Male | 74 | 18 |
| 3 | Gastric ac | Male | 47 | 19 |
| 4 | Gastric gej | Male | 64 | 20 |
| 3 | Pancreas | Female | 57 | 21 |
| 4 | Pancreas | Male | 58 | 22 |
| 4 | Prostate | Male | 77 | 23 |
| 1 | Thyroid | Female | 54 | 24 |
| 2 | Cervix | Female | 35 | 25 |

C. Blood Samples Transport

Measures are taken to keep the viability of the blood cells at thermo-stated conditions (Thermo Electric cooling (down to 10° C.-18° C.) and gently shaking till the PBMCs separation.

$D_1$. Peripheral Blood Mononuclear Cells (PBMCs) Separation

Fresh peripheral blood mononuclear cells (PBMCs) were isolated by Ficoll-Paque (UNI-SEP, Novamed) and gradient centrifugation. The pellet was resuspended in working solution (WS) (PBS with calcium and magnesium) including the fluorescent probe (HPTS) at a final concentration of $5 \times 10^6$ cells/ml.

$D_2$. High Throughput Parallel Measurements of the MA Test

Each well in a black non-binding, low-volume 384 multi-well plate (Greiner Bio-One) was loaded with 10 μl of the PBMCs solution and 10 μl of working solution plus HPTS including one of ten reagents in 8 increasing concentrations. Thus the final concentration of the probe in each well was 1 μM, and the final concentration of the PBMCs was $2.5 \times 10^6$ cells/ml in 20 μl physiological working solution containing 10 mM phosphate buffer around pH 7.3. Taking into account the average PBMCs concentration in adult peripheral blood a working concentration of 2.5×10⁶ cells/ml was selected. This concentration of PBMCs is considered to ensure two aspects: first, to get a reasonable signal-to-noise ratio due to product accumulation during at least 1 hour, and second, to allow for intercellular interaction. The same protocol of 10 µl loading was carried out at least in triplicates, first on the PBMCs samples and then on the reagents, so as to accurately obtain the final 20 µl volume in the required concentration in each well. Furthermore, in each test two types of controls were included: one including only the probe (1 µM), without cells and without the stimulants in 8 wells; the other one including only cells without a stimulant, basal state, in 8 wells. The acidification process was monitored each 5 min during 1 hour of incubation at 37° C. by a commercial fluorescence scanner (TECAN Infinite M200). First, the scanner monitored the acidification process without sealing ("OPEN" mode) during 30 min (6 cycles) and then, to avoid ventilation of $CO_2$ and $NH_3$ from each well, the multi-well plate was sealed hermetically (ThermalSeal RT™, EXCEL Scientific, Inc.) ("CLOSE" mode). Next, the acidification process was monitored again during 30 min (6 cycles). In order to increase the signal to noise ratio, the fluorescence intensities at 513 nm were measured sequentially under excitation at 455 nm and 403 nm per well.

In order to quantify the sensitivity of the probe, a stock solution of HPTS was diluted in water to a concentration of 100 µM and then to a final concentration of 1 µM and 10 µM. WS acidity calibration was made for two buffer concentrations: the WS (10 mM phosphate buffer) and the WS diluted 5 times by saline (2 mM phosphate buffer) (FIGS. 3A-D, FIGS. 4A-B).

The final calibration curve used in the MA test was carried out by pH-glass electrode measurements of sequential titration of WS (containing 2 µM HPTS). The pH measurements and the fluorescence measurements of the titrated samples are carried out at 37° C. The samples are loaded into a multi-well plate and the fluorescence intensities under EX403 nm and EX455 nm are measured at 513 nm using the fluorescence scanner.

For the "OPEN" and "CLOSE" states, a calibration polynomial curve is constructed (FIGS. 3C-D), allowing to measure pH values and accumulated acidification equivalents as a function of the ratio between the fluorescence intensities measured at 513 nm, under excitations at 403 nm and 455 nm, respectively.

The equations obtained were used for analysis of every new donor (Table 3, below).

TABLE 3

The equations obtained from the final calibration curves:
X = Fluorescence intensity at Ex. 403 nm/Fluorescence Intensity at Ex. 455 nm

| | pH | HCI (µmol/ml) |
|---|---|---|
| Open | $Y = 0.011X^4 - 0.136X^3 + 0.641X^2 - 1.528X + 8.266$ | $Y = 0.006X^4 + 0.129X^3 - 0.982X^2 + 3.971X - 2.276$ |
| Close | $Y = 0.013X^4 - 0.164X^3 + 0.747X^2 - 1.723X + 8.415$ | $Y = -0.006X^4 + 0.131X^3 - 1.011X^2 + 4.168X - 2.581$ |

$D_3$. Type, Spectrum and Preparation of Reagents

In each test, the metabolic activity profiles of PBMCs were monitored in the basal state and under the influence of the following ten reagents diluted in working solution in 8 different concentrations: PHA, CONA, PMA, LPS, MBP (28), MelanA, PSA(29), Glucose(24), L-glutamine and Rapamycin (Strauss L, Czystowska M, Szajnik M, Mandapathil M, & Whiteside T L (2009) Differential responses of human regulatory T cells (Treg) and effector T cells to rapamycin. *PLoS One* 4(6):e5994.). The reagents selection was made by their relation to the immune system (TABLE 1, above, note, concentrations are not limited to those in the table, concentration=0 to non toxic dose).

It should be mentioned that other reagents are under calibration, for example: (hormones such as estradiol, cancer specific antigens such as carcinoembryonic antigen (CEA), cytokines and chemokines such as il-2, vitamins, hormones, drugs, antibodies of the immune system, neurotransmitters, different cancer peptides and specific viruses or their fragments such as human papilomavirus (HPV) (data not shown).

$D_4$. Ratiometric Measurement of the pH Sensitive Fluorescent Probe and WS Acidity Calibration The probe used in this test is 8-Hydroxypyrene-1,3,6-trisulfonic acid (HPTS).

HPTS is a cost effective, non-toxic, highly water-soluble membrane-impermeant pH indicator with a pKa of ~7.3 in aqueous buffers. HPTS exhibits a pH-dependent absorption shift, allowing ratiometric pH measurements as function of the ratio between the fluorescence intensities at 513 nm that are measured sequentially under excitation at 455 nm and 403 nm. This method is essential for the present sensitive measurements of minor pH changes in the physiological range around pH 7.

E. Data Analysis

Computation, analysis and data mining (Nisbet R, I V J E, & Miner G (2009) *Handbook of Statistical Analysis and Data Mining Applications*) were done by using the following Statistical Package; EXCEL 2007, OriginPro 8, SAS Edition 9.2, PASW Modular client 13.0 (formally called Clementine, part of SPSS). Results in FIGS. 6A-C-8A-D, 13 are expressed as means±standard error of the mean. Statistical significance between healthy and cancer patients for variant models was calculated using chi-square. Results were considered statistically different when p<0.05.

Donor's Data Analysis (Summarized in Flowchart of the MA Test Framework—FIG. 12)

Data Preparation—

Step 0: Processing and Normalizing Donor Data

The raw data of each record (donor) was processed to yield the results in terms of the acidification rate of metabolic activity in units of pmole $H^+$/µl/hour/2500PBMCs.

Pre Processing—Step 1a: Probe Analysis and Donor Data Normalization

In order to improve the signal to noise ratio, analysis of probe was done by performing k-means cluster analysis on all observations (n=730) collected from all donors (FIGS. 5A-D). These processed results were normalized by subtracting the donor values from the HPTS mean values after removal of probe's outliers (not more than 5% of the results were removed).

Pre Processing—Step 1b: Excluded Outliers in Donor's Data

Normalizing "OPEN" and "CLOSE" values by the mean values of "OPEN" and "CLOSE" for each combination of donor, dose and stimulant. Observations with standard score>|1.7| were discarded (1.77% of the results).

Data Preparation—Step 1c: Representation of Donor Metabolic Activity Results

After removing the outliers in each donor, average values of "OPEN" and "CLOSE" were calculated separately for each donor based on the average of at least triplicate results for each dose and each reagent per donor. These results would be used later as representing donor metabolic activity for each reagent and dose. The results were planted in 2D graphs and 3D graphs and would be updated automatically with every donor.

Searching for Classification Model—Step 2: Data Mining Algorithm

Since most of the studied cancer patients were older than 39 and in order to minimize as much as possible the effect of age, two cohorts of blood donors including males and females were tested and analyzed. The first cohort includes donors with the age above 40 (n=42 (21 healthy donors and 21 cancer patients)) and the second cohort include the full set of donors (n=67 (42 healthy donors and 25 cancer patients)) from 22-81 years old. For Classification of the step 3 results a set of algorithms from a family of Decision Trees/Rule Induction (C5, CART, CHAID, ASSOCIATION RULE) and log linear model (Logistic Regression) was used. Exploratory analysis methods were used to investigate hidden and unhidden connections in the data.

Model Evaluation—Step 3: Model Building and Classification

For classifying the donors into healthy and cancer patients, a set from the family of ten different models including data mining, machine learning and statistical modeling were used applying SAS 9.3 and Clementine software (V13.0). In order to evaluate and compare the performance of the models it was decided to use the graphical method which is based on the cumulative gain charts produce by Clementine software (V13.0) (FIGS. 9A-D).

Predictive Modeling—Step 4: Evaluation Using a Validation Set of 30% of Blood's Donors Data as described in step 3 was randomly partitioned into two groups of "Training" and "Testing" using the Clementine software (V13.0). The "Training set" are used to build the data mining model and includes 70% of the donors. The remaining 30% of the donors will be used to evaluate the classification result on the "Testing" set using the models that were generated in the Training set (FIGS. 10A-D).

The whole data analysis process is summarized in the Flowchart of the MA test protocol and analysis Framework (FIG. 12).

Example 2

MA Test Design and Characteristics

Fresh peripheral blood mononuclear cells (hPBMCs) were isolated by Ficoll-Paque and gradient centrifugation from 42 healthy donors and 25 cancer patients (TABLE 2, above). For each blood sample, a 384 multi-well plate was loaded with 20 µl containing physiological working solution at 10 mM buffer around pH 7.3, hPBMCs at final concentration of ~2.5×10$^6$ cells/ml, 1 µM pH probe (HPTS), and one of ten stimulating reagents in eight increasing concentrations (TABLE 3, above). The MA test is carried out using a commercial fluorescence scanner. The extracellular acidity kinetic profiles were measured either under air-open ("OPEN") or hermetically-sealed closed ("CLOSE") states. Both records enable to measure the real-time accumulations of 'soluble' versus 'volatile' metabolic products (lactic acid versus $CO_2$ and $NH_3$), thereby differentiating between oxidative phosphorylation, anaerobic glycolysis and aerobic glycolysis ("Warburg effect")(Vander Heiden M G, Cantley L C, & Thompson C B (2009) Understanding the Warburg effect: the metabolic requirements of cell proliferation. *Science* 324(5930):1029-1033). The MA rate profiles were calculated and examined for cancer diagnosis by dynamic online analysis, including data mining tools (FIG. 12).

Example 3

Ratiometric Fluorescence Extracellular pH Measurement and Acidity Calibration

The non-toxic, membrane-impermeant, ratiometric molecular pH-probe used in the present MA test is 8-hydroxypyrene-1,3,6-trisulfonic acid (HPTS) (Hakonen A & Hulth S (2008) A high-precision ratiometric fluorosensor for pH: implementing time-dependent non-linear calibration protocols for drift compensation. *Anal Chim Acta* 606(1): 63-71; Han J & Burgess K (Fluorescent indicators for intracellular pH. *Chem Rev* 110(5):2709-2728) with a $pK_a$ of ~7.3 in aqueous physiological buffers. It is well-known by its low-toxicity, from intracellular pH measurements in many cell types, even under overnight incubation at 2 mM (Overly C C, Lee K D, Berthiaume E, & Hollenbeck P J (1995) Quantitative measurement of intraorganelle pH in the endosomal-lysosomal pathway in neurons by using ratiometric imaging with pyranine. *Proc Natl Acad Sci USA* 92(8):3156-3160). Here, HPTS is rather used for extracellular pH measurements, at a low 1 µM concentration, which further ensure its non-toxicity. Calibration polynomial curves were constructed for the "OPEN" and "CLOSE" states, (FIGS. 3A-D), allowing to measure pH values and accumulated acidification equivalents as a function of the ratio between the fluorescence intensities measured at 513 nm, under excitations at 403 nm and 455 nm, respectively. The acidification calibration curves were obtained for the working solution (WS) and for the WS diluted 5 times with saline (10 mM and 2 mM phosphate buffer, respectively) (FIGS. 3A-D). As expected, this figure verifies that the 10 mM buffer capacity allows for about five times of the acidification values compared to that of the 2 mM buffer capacity, within the same range of pH changes. These results indicate on the proper sensitivity to acidification within the physiological pH range 6.5-7.5. Further results indicate that the measurement method is independent of the fluorescent probe concentration between 1-10 µM. The system is sensitive enough to provide a high signal-to-noise ratio when the extracellular final concentration of HPTS is only 1 µM (FIGS. 4A-B).

The equations obtained from the final calibration curves (FIGS. 3A-D, TABLE 4) were used for quantitative analysis of the significant measured changes in PBMCs metabolic activity records from all 67 donors (42 healthy and 25 cancer patients).

Example 4

Improving Signal-to-Noise Ratio by Dynamic K-MEANS Cluster Analysis of HPTS Background Aiming at dynamic clinical evaluation of the MA test results, a reliable method was developed that compares any MA test for each donor to previous tests with respect to the reference rate values of the HPTS signal (n=730 observations). By this data collection it is possible to improve the signal to noise ratio of the MA test by filtering exceptional reference results. For that purpose k-means cluster analysis (Nisbet R, I V J E, & Miner G (2009) *Handbook of Statistical Analysis and Data Mining Applications*) was applied for the accumulating normalized rate values of the HPTS probe. In each test at least eight control wells were examined, containing 1 µM HPTS in the working solution, without cells and without stimulants. Each value was normalized taking into account the accumulated observations using a standard score. FIG. 5A presents the distribution of the standard scores for "OPEN" and "CLOSE" rate values of all MA tests. By k-means cluster analysis 26 clusters were obtained (FIG. 5B), where each observation belongs to the cluster with the nearest mean. The results reported in FIG. 5D evaluate the stable performance of the probe. Out of all HPTS reference results (n=730) only 5 clusters (4.66%) were discarded. The rest 21 clusters (95.34%) were finally considered to compose the normal reference range. The mean values of "OPEN" and mean values of "CLOSE" states were recalculated for each donor. The k-means cluster analysis allows us to extract the probe background rate signal from the cellular data and thereby get the actual rate values of the ongoing MA test results.

Example 5

MA Profiles of Control Samples: (i) at Increasing Reagents Concentrations in the Absence of Cells; (ii) with Cells but No Reagents (i) Control experiments in the absence of cells verified that the acidification profiles obtained in the presence of cells indeed measure the rate of cellular metabolic activity. Thus, no acidification was obtained under the same protocol applied in the presence of probe, buffer and each reagent at increasing concentration, but with no cells (e.g glucose (FIG. 6A) and PSA (FIG. 8A)), compared to clear acidification changes in samples with cells. The same control results were obtained for all reagents. (ii) A basal level of acidification in the presence of cells was measured in the absence of any reagents including glucose. Generally, this basal level increased with increasing glucose concentrations, verifying clear aspects of cellular metabolic activity (FIGS. 6B-C). Moreover the MA profiles at the basal state already revealed the general trend of a diagnostic shift from dominant oxidative phosphorylation preferred by the naive hPBMCs of 69% of the healthy donors, to dominant aerobic glycolysis ("Warburg effect") preferred by activated hPBMCs of 60% of various cancer patients. These results emphasize the potential of the MA-test as a diagnostic tool already at the basal state which is the closer scenario to the in vivo state. However the basal state alone is not enough for clear cut differentiation between healthy and cancer patients (Chi-Square, p=0.45). By the present data mining of all the MA-test profiles in response to network of reagents reagents (FIGS. 10A-D), it can significantly point on 95.24% of healthy donors and 88% of cancer patients (age≥4° Chi-Square, p<0.0001) and on 90.48% of healthy donors and 95.24% of cancer patients (22≤age≥81, Chi-Square, p<0.0001).

Example 6

Comparison of MA Profiles at Increasing Glucose Concentration, Obtained for Typical Healthy Donor and Breast Cancer Patient First, MA profiles of healthy donors (FIGS. 6B, 7A) are strikingly similar, despite the significant difference in age (45 (FIG. 6B) vs. 69 (FIG. 7A)) and gender. Second, the results in FIG. 6A-C reveal significant MA profiles differences between two donors that represent a typical healthy donor and a breast in situ cancer patient (at stage 2, and before any treatment). Additionally, in preliminary experiments where the MA test was applied on few cases of auto-immune diseases and additional non-cancer related infectious diseases, different metabolic activity profiles compared to those obtained for healthy individuals and cancer patients (data not shown) were already revealed. These differences point on 3 clinical diagnostic indexes of cancer (FIGS. 4A-C). Index 1: MA rate "OPEN">MA rate "CLOSE" in the basal state (cells in working solution without reagent). Index 2: MA rate "OPEN">MA rate "CLOSE" for all glucose concentrations. Index 3: MA rate "OPEN" of cancer>MA rate "OPEN" of healthy and MA rate "CLOSE" of cancer>MA rate "CLOSE" of healthy. Thus, higher values of oxidative phosphorylation are obtained in fresh PBMCs of healthy samples compared to higher values of aerobic glycolysis in fresh PBMCs of cancer samples. As mentioned in the introduction (Vander Heiden M G, Cantley L C, & Thompson C B (2009) Understanding the Warburg effect: the metabolic requirements of cell proliferation. *Science* 324(5930):1029-1033; Fox C J, Hammerman P S, & Thompson C B (2005) Fuel feeds function: energy metabolism and the T-cell response. *Nat Rev Immunol* 5(11):844-852; Michalek R D & Rathmell J C (The metabolic life and times of a T-cell. *Immunol Rev* 236:190-202) these results presumably indicate on in vivo development of the "Warburg Effect" in activated hPBMCs of cancer patients. More detailed observations on the MA test results obtained for cancer patients (FIG. 6C and FIGS. 7B-D) reveal that in the "CLOSE" state the total acidification rate is less than in "OPEN" state. These results indicate on a volatile basic product which is responsible for partial titration of the acidity due to lactic acid and $CO_2$. This titration might be physiologically required upon the metabolic switch to the non-volatile lactic acid production. This role is related to ammonia ($NH_3$), which is one of the primary products of protein catabolism and metabolic pathways of purines and pyrimidines. In the instant measurement system, as in-vivo, vital cells must maintain the cytoplasm in a constant pH of about 7.2-7.4 by simultaneous metabolic secretion of both the acidic and basic products as described below.

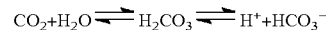

It should be mentioned that in the 3 indexes analysis, different combinations were found at different stages of various cancers (e.g. colon, breast, lung, and pancreas) (TABLE 2, above). Therefore, by these variations it is believed that the examination of enough data collection and follow-up of individual donors will provide reliable and more informative diagnostic profiles, as demonstrated in the following case study (FIGS. 7A-D).

Example 7

Case Study Follow-Up of MA Profiles, at Increasing Glucose Concentration, Obtained for a 65 Years Old Female with Breast Cancer With respect to the preliminary MA-test measurements, it should be mentioned that one case of thyroid cancer and one of breast cancer were diagnosed by the present test before the physicians. The breast cancer case was followed up along two years as evidence for the sensitive informative capability of the MA test compared to typical classification of staging and treatments. This is the first report of a 2 years follow-up study of a female donor, clinically diagnosed to have breast cancer one year after the MA test had revealed a state of cancer. For comparison, MA profiles are presented of a typical healthy 69 years old male (FIG. 7A). MA profiles of the cancer patient on TIME ZERO, the patient clinically diagnosed as having breast cancer one year after the MA test had revealed a state of cancer (I.E.,) (FIG. 7B). The three cancer diagnostic indexes indicate on a shift from oxidative phosphorylation observed in the healthy profiles (FIG. 7A) to aerobic glycolysis observed in the cancer case profiles (FIG. 7B). Namely, positive values for "CLOSE-OPEN" of healthy profiles (FIG. 7A) and negative values for "CLOSE-OPEN" obtained for the cancer profiles (FIG. 7B). The next MA test obtained for this study case was carried out 10.5 months later (FIG. 7C), just after routine mammography diagnosis of breast idc cancer at stage 2. It should be emphasized that at that time the patient didn't report any physiological or palpable symptoms.

From this point on, a follow-up MA test was carried out every 3 weeks. One month later, a tumor surgical removal was carried out. Another month later a chemotherapy treatment was given every 3 weeks. Each MA test was carried out after about 20 days of each treatment, and 2 days before the next treatment. The last MA test presented here (FIG. 7D) was carried out after the third chemotherapy treatment, namely about 2 months after beginning the chemotherapy protocol (time=(+)14.5 months). It should be noticed that according to the three indexes of the MA test, this last test already reveals MA profiles (FIG. 7D) characteristic of healthy donor (FIG. 7A). Obviously the MA test verifies a positive trend along with the ongoing treatment. By these results, it will be important to use the MA test in a follow-up procedure in order to reveal the trend behavior of the MA test profile compared to clinical evaluation during and far behind completion of the chemotherapy treatment. This follow-up program is made available by the clinically-oriented MA test which is simple, non-invasive and non-expensive.

Example 8

Comparison of MA Profiles, at Increasing PSA Concentrations, Obtained for Typical Healthy, Breast Cancer Patient and Breast Cancer-Recovered Donor Up till now the MA profiles were examined under increasing concentration of glucose that were clearly found as a general non-specific clinical tool for cancer diagnosis. In order to gain more specific cancer classification, the MA test explores simultaneously various reagents (TABLE 3) such as tissue-specific normal antigens (e.g PSA, MelanA).

Prostate-specific antigen (PSA) is a normal protein produced by cells of the prostate gland. The PSA is a cancer-associated tissue-specific normal antigen. This peptide is recognized by cytotoxic T lymphocytes (CTL). Increasing level in human peripheral blood of this peptide is clinically used as a biochemical diagnostic marker of prostate cancer for men (Greene K L, et al. (2009) Prostate specific antigen best practice statement: 2009 update. *J Urol* 182(5):2232-2241). But, low levels of PSA are released into the female circulation and up to date the clinical PSA blood test is not used as a diagnostic factor for women. However, numerous studies have shown that PSA is not prostate specific, but is present in some female hormonally regulated tissues, principally the breast and its secretions (Black M H & Diamandis E P (2000) The diagnostic and prognostic utility of prostate-specific antigen for diseases of the breast. *Breast Cancer Res Treat* 59(1):1-14; Black M H, et al. (2000) Serum total and free prostate-specific antigen for breast cancer diagnosis in women. *Clin Cancer Res* 6(2):467-473). In women, PSA is found in female ejaculate at concentration roughly equal to that found in male semen (Wimpis singer F, Stifter K, Grin W, & Stackl W (2007) The female prostate revisited: perineal ultrasound and biochemical studies of female ejaculate. *J Sex Med* 4(5):1388-1393; discussion 1393). Three MA profiles are presented in FIGS. 8A-D, a typical healthy woman (FIG. 8B), woman with breast cancer idc in stage 2 and before treatment (FIG. 8C), and female recovered from stage 2 breast cancer 18 years ago (FIG. 8D). Tissue-specific stimulants e.g PSA are observed to induce marked peaks at optimal concentrations in the MA-test profiles of cancer patients (FIGS. 8A-D). Such profiles are considered to reflect disease-specific receptor-mediated stimulation and thereby enable to detect specific tumors (e.g breast by PSA, melanoma by melanA stimulation). The results reveal several significant issues. First, the MA profile of healthy women indicate a higher level of oxidative phosphorylation as already reported above for glucose MA profiles (FIGS. 6A-C and FIGS. 7A-D). Second, FIG. 8C point on a PBMCs response to PSA by a female with breast idc cancer in stage 2, before any treatment. This profile expresses high metabolic activity rate at the "OPEN" state, already from the basal state. These profiles indicate a high level of aerobic glycolysis, a phenomena which is similar to activated T-cells as obtained for the glucose MA profiles of cancer patients. Another unique profile of the MA test was revealed for 50 years old female recovered from breast cancer 18 years ago (FIG. 8D). This profile for PSA stimulation behaves more like that of healthy donor (FIG. 8B). Furthermore it reveals higher MA rate in "close" state that indicates a dominant oxidiative phosphorylation pathway at increasing PSA concentrations more than the characteristic profile for healthy donor (FIG. 8B). This profile maybe related to an increased population of anti-breast cancer memory cells. This relation is consistent with the observation that following pathogen clearance, surviving effector cells differentiate into long-lived memory cells and revert to an oxidative metabolic state (Michalek R D & Rathmell J C (The metabolic life and times of a T-cell. Immunol Rev 236:190-202).

Example 9

Model Building and Classification Evaluation for the MA Test Results by Data Mining Tools Multiple MA profiles including a huge number of MA rate values are obtained for each donor. In order to develop a dynamic clinical analysis that is updated with every new donor, and to extract patterns from this large data base, a computer programming using Data Mining tools were developed, which combine methods from statistics and artificial intelligence with database management (Nisbet R, I V J E, & Miner G (2009) *Handbook of Statistical Analysis and Data Mining Applications*). Two selected cohorts of the MA test results, for both males and females, were analyzed. Since most of the cancer patients studied were older than 39, and in order to minimize as much as possible the effect of age, this analysis focused on a subgroup of 42 donors with the age above 40 (21 healthy donors and 21 cancer patients). In the second cohort the full set of donors were used from 22-81 years old (n=67, 42 healthy donors and 25 cancer patients). In order to classify the donors into healthy and cancer individuals, a set from the family of ten different models including data mining, machine learning and statistical modeling, applying SAS 9.3 and Clementine software (V13.0) were used. Out of these ten models, only four were able to classify with the highest accuracy both healthy donors and cancer patients. Out of the four models, three were from the family of decision tree (CHAID, C5, C&R TREE) and one of log linear model (Logistic Regression). All four are presented in FIGS. 9A-D. The decision-tree models are considered to be the best classifiers, since these models don't assume any distributions or any assumptions. The fourth model that didn't perform as good as the others is the Logistic regression. This kind of model is best suited when input data behaves exactly as the assumptions of the model, such as assumptions about distribution and independency. In order to minimize as much as possible over-fitting the Logistic Regression model was ran using the forward selection method, which enabled us to order the variables by importance and minimize as much as possible the number of selected variables. Since each model shows different variables/features as a function of different antigens, each at different concentrations, it may be possible to combine the present predictions as a function of more than one model. When examining the influence of the overall reagents in different concentrations on the accuracy of the models, the maximal number of variables that were chosen was not more than five (FIGS. 9A,9C), which is recommended when sample size is not sufficient to minimize as much as possible the over-fitting. By these initial results it was possible to order the ten reagents as predictors by their frequency of appearance in the various models (FIGS. 9A, 9C). Currently it is possible to pinpoint glucose, MBP, Rapamycin, PSA and PMA as pivotal players in the MA test and in relation to the immune system (TABLE 3). The immunological relevance of the other five reagents (TABLE 3) is still revealed by the occasional models' choice. In order to evaluate and compare the performance of the models, the present inventors decided to use the graphical method which is based on the cumulative gain charts produced by Clementine software (V13.0). The gain chart (FIGS. 9B, D) contains two built-in curves, the random curve (black line) and the best fit curve (sky blue line). All models fall between these two curves. In this method, greater area between a given curve and the random curve (black curve) indicate on a better model. Blood's donors modeling and classification results point on models with performance similar to the best model (FIGS. 9A-D).

Example 10

Evaluating Model Results of the MA Test Using a Validation Set of 30% of Blood's Donors A partition process described below enables to combine and compare models so as to gain more confidence in the accuracy of the MA test results, to evaluate the robust level of the models, and to minimize over-fitting due to small sampling (n=67 blood sample donations). The data as described in FIGS. 9A-D was randomly partitioned into two groups of "Training" and "Testing" using the Clementine software V13.0 9 (FIGS. 10A-D). The validation set included 70% of the donors for both cohorts. First cohort includes 42 donors with the age above 40 (FIGS. 10A-B) and the second cohort includes full set of donors (n=67) from 22-81 years old (FIGS. 10C-D). The first 70% of the donors are described on the "Training set". The "Training set" is used to build the data mining model as described in FIGS. 9A-D. The remaining 30% of the donors ("Testing set") enable to evaluate the classification result on the "Testing set" using the models that were generated in the "Training set" (CHAID, Logistic, C5, C&R tree) (FIGS. 10A. C). The "Training" and "Testing" sets enable to evaluate model results with greater confidence and eliminate as much as possible the over fitting challenge. In both cohorts it was found that C5 model gave more robust results where the "Testing" set curve was similar to the "Training" set (FIGS. 10B, D). C5 model was the best performer in the "Testing" set while in the "Training" set C&R tree was the best performer. By these results it is possible to pinpoint glucose, MBP, PMA, PHA, CONA and L-Glutamine as pivotal players in the MA test and in relation to the immune system (TABLE 3). Similarly to the best models in FIGS. 9A-D, these results (FIGS. 10A-D) support the results of FIGS. 9A-D.

A physiological approach to cancer diagnosis is presented here by relying on the preliminary experimental results of the metabolic activity profiles obtained for hPBMCs of healthy and cancer patients. By this approach the present inventors have designed a simple high-throughput, short-time and cost effective optical method of the MA test using fresh hPBMCs extracted from 10-20 ml blood sample. Striking differences of hPBMCs fingerprinting MA patterns were revealed by preliminary examination of two clinical groups, 42 healthy individuals and 25 cancer patients. While the hPBMCs MA profiles of the 42 healthy donors indicate a similar preferred oxidative phosphorylation pathway, the hPBMCs of the 25 cancer patients have a wide spectrum of MA profiles, preferring aerobic glycolysis in correlation with staging and treatment. One case of thyroid cancer and one of breast cancer were diagnosed by the MA test before the physicians. This breast cancer case was followed up by the MA test along two years as evidence for the sensitive informative capability of the MA test with respect to typical classification of staging and treatments.

The results reported here, encourage further exploration of the metabolic activity of hPBMCs as a mirror image of tumor development (FIGS. 9A-D). Preliminary results clearly reflect common, as well as specific, features of hPBMCs metabolic pathways under cancer-induced evasion of the immune system during the pathological development of different tumors.

A tissue-specific cancer diagnostic index may be provided by the MA-test profiles at early and late stages of local tumor development by increase (or decrease) of the MA rates relative to those observed for healthy donors. Certain optimal concentrations of tissue-specific antigens should be sought for the MA-test profiles. Such tissue-specific diagnostic profiles are expected also at early stages of tumor development, when initial aggressive antitumor immune response is anticipated. By this approach, it can be postulated that in the healthy state, the immune system is responsible for ongoing early detection and effective eradication of cancer cells in the context of its normal function, by scrutinizing all body tissues. The immune system is therefore proposed to detect and eliminate cancer cells by their excessive expression of tissue-specific normal antigens. Therefore, in homeostasis, a balanced level of an effective immune response should be well controlled, so as to avoid either a decline of effective cytolytic function, or such aggressive activity against self normal cells that might rather precipitate autoimmune diseases. Thus, unfortunately, in advanced stages of cancer the immune system is known to be suppressed, or even educated to support cancer development by tumor-infiltrating lymphocytes, which might be a part of the circulating hPBMCs. In this view, it is further anticipated that at the lethal metastatic phase of cancer the MA-test profiles of hPBMCs might shift back to reflect an apparent healthy state due to tissue-specific immunity tolerance and anergy, unlike in chronic inflammation. This apparent healthy state may be exposed by exhaustion of the relevant tissue-specific antigen stimulation.

Example 11

PBMCs Metabolic-Activity Profiles for Increasing Glucose Concentration Obtained for Typical Healthy, Cancer and Autoimmune Lupus Donors In homeostasis, the immune system activity should be well controlled; hyperactivity is associated with autoimmune diseases while cancer development is probably related to hypoactivity of the immune system.

Significantly different MA Profiles were obtained for increasing glucose concentration obtained for typical healthy, cancer, and autoimmune lupus donors (FIG. 13).

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

REFERENCES

Other References are Listed Throughout the Application

1. Bassani-Sternberg, M. et al. Feature Article: Soluble plasma HLA peptidome as a potential source for cancer biomarkers. *Proc Natl Acad Sci USA*.
2. Hayden, E. C. Personalized cancer therapy gets closer. *Nature* 458, 131-2 (2009).
3. Kawakami, Y. et al. Identification of human tumor antigens and its implications for diagnosis and treatment of cancer. *Cancer Sci* 95, 784-91 (2004).
4. Robins, H. S. et al. Overlap and effective size of the human CD8+ T cell receptor repertoire. *Sci Transl Med* 2, 47ra64 (2010).
5. Early warnings. *Nature* 458, 679 (2009).
6. Sawyers, C. L. The cancer biomarker problem. *Nature* 452, 548-52 (2008).
7. Luebeck, E. G. Cancer: Genomic evolution of metastasis. *Nature* 467, 1053-5.
8. Rosenberg, S. A. & Dudley, M. E. Adoptive cell therapy for the treatment of patients with metastatic melanoma. *Curr Opin Immunol* 21, 233-40 (2009).
9. Rosenberg, S. A., Restifo, N. P., Yang, J. C., Morgan, R. A. & Dudley, M. E. Adoptive cell transfer: a clinical path to effective cancer immunotherapy. *Nat Rev Cancer* 8, 299-308 (2008).
10. Terme, M., Ullrich, E., Delahaye, N. F., Chaput, N. & Zitvogel, L. Natural killer cell-directed therapies: moving from unexpected results to successful strategies. *Nat Immunol* 9, 486-94 (2008).
11. An autoimmune-mediated strategy for prophylactic breast cancer vaccination. *Womens Health (Lond Engl)* 6, 493.
12. Alexander-Miller, M. A. High-avidity CD8+ T cells: optimal soldiers in the war against viruses and tumors. *Immunol Res* 31, 13-24 (2005).
13. Michalek, R. D. & Rathmell, J. C. The metabolic life and times of a T-cell. *Immunol Rev* 236, 190-202.
14. Maciver, N. J. et al. Glucose metabolism in lymphocytes is a regulated process with significant effects on immune cell function and survival. *J Leukoc Biol* 84, 949-57 (2008).
15. Zhang, Q. Y. et al. Myelin-basic protein-reactive specific CD4+ and CD8+ NK lymphocytes induce morphological changes in neuronal cell bodies and myelin sheaths: implications for multiple sclerosis. *Arch Med Res* 39, 45-51 (2008).
16. Narita, D., Cimpean, A. M., Anghel, A. & Raica, M. Prostate-specific antigen value as a marker in breast cancer. *Neoplasma* 53, 161-7 (2006).
17. Bromley, S. K., Mempel, T. R. & Luster, A. D. Orchestrating the orchestrators: chemokines in control of T cell traffic. *Nat Immunol* 9, 970-80 (2008).
18. Kaelin, W. G., Jr. & Thompson, C. B. Q&A: Cancer: clues from cell metabolism. *Nature* 465, 562-4.
19. Fox, C. J., Hammerman, P. S. & Thompson, C. B. Fuel feeds function: energy metabolism and the T-cell response. *Nat Rev Immunol* 5, 844-52 (2005).
20. Vander Heiden, M. G., Cantley, L. C. & Thompson, C. B. Understanding the Warburg effect: the metabolic requirements of cell proliferation. *Science* 324, 1029-33 (2009).
21. Nisbet, R., I V, J. E. & Miner, G. *Handbook of Statistical Analysis and Data Mining Applications* (ed. Material, C.) (2009).
22. Patolsky, F. et al. Electrical detection of single viruses. *Proc Natl Acad Sci USA* 101, 14017-22 (2004).
23. Zheng, G., Patolsky, F., Cui, Y., Wang, W. U. & Lieber, C. M. Multiplexed electrical detection of cancer markers with nanowire sensor arrays. *Nat Biotechnol* 23, 1294-301 (2005).
24. Hakonen, A. & Hulth, S. A high-precision ratiometric fluorosensor for pH: implementing time-dependent non-linear calibration protocols for drift compensation. *Anal Chim Acta* 606, 63-71 (2008).

What is claimed is:

1. A method of diagnosing and treating solid cancer in a subject-in-need thereof, the method comprising:
   (a) providing a biological sample of the subject which comprises non-pathogenic lymphocytes;
   (b) measuring acidification in an extracellular defined solution having a calibrated buffered capacity of said non-pathogenic lymphocytes in a time-dependent manner so as to generate a time dependent acidification profile,
   wherein said at least one time dependent acidification profile is due to secretion of:
   (i) non-volatile soluble metabolic products and volatile soluble metabolic products;

(ii) non-volatile soluble metabolic products; or
(iii) volatile soluble metabolic products,
wherein measuring acidification profile of said (ii) is effected in an air-exposed chamber, and wherein measuring acidification profile of said (i) is effected in an air-sealed chamber, and wherein measuring acidification profile of said (iii) is by subtracting an acidification profile of said (ii) from an acidification profile of said (i), wherein a statistically significant change in said time dependent acidification profile as compared to that in a control unaffected sample obtained under identical conditions, is indicative of a solid cancer diagnosis; and (c) treating the subject with an anti cancer agent to the solid tumor.

2. The method of claim 1, wherein said buffer comprises a phosphate buffered saline.

3. The method of claim 1, wherein said measuring is effected using a non-toxic membrane impermeable probe selected from the group consisting of a pH probe, a $CO_2$ probe and $NH_3$ probe and a lactate probe.

4. The method of claim 3, wherein said pH probe comprises a ratiometric pH probe.

5. The method of claim 4, wherein said pH probe comprises HPTS.

6. The method of claim 1, wherein said non-volatile metabolites comprise lactate.

7. The method of claim 1, wherein said volatile metabolites comprise $NH_3$ and $CO_2$.

8. The method of claim 1, wherein said measuring said acidification profile is effected at a constant temperature.

9. The method of claim 8, wherein said constant temperature comprises 37° C.

10. The method of claim 1, further comprising subjecting said non-pathogenic lymphocytes to a stimulant or inhibitor prior to, or concomitant with measuring said acidification profile, wherein said stimulant or inhibitor increases, decreases or changes a metabolic pathway of said non-pathogenic lymphocytes in response thereto.

11. The method of claim 10, wherein said stimulant or inhibitor comprises a cell.

12. The method of claim 10, wherein said stimulant or inhibitor comprises a cell-free antigen.

13. The method of claim 11, wherein said stimulating cell comprises a lymphocytes and said cell comprises a non-syngeneic lymphocyte with respect to said lymphocyte.

14. The method of claim 1, wherein said measuring said acidification profile is effected in a commercial fluorescence multi well plate scanner.

* * * * *